United States Patent
Zannis et al.

(10) Patent No.: US 7,559,941 B2
(45) Date of Patent: Jul. 14, 2009

(54) INSTRUMENT FOR DELIVERY OF IMPLANT

(75) Inventors: Anthony D. Zannis, Fort Wayne, IN (US); John W. Kemppainen, Richland, MI (US); Andrew M. Jacobs, Fort Wayne, IN (US); Carolyn K. Day, Maumee, OH (US); Rhonda B. Clarke, Winona Lake, IN (US); Herbert E. Schwartz, Ft. Wayne, IN (US); Prasanna Malaviya, Ft. Wayne, IN (US); Danny E. McAdams, Ft. Wayne, IN (US)

(73) Assignee: Depuy Products, Inc., Warsaw, IN (US)

( * ) Notice: Subject to any disclaimer, the term of this patent is extended or adjusted under 35 U.S.C. 154(b) by 974 days.

(21) Appl. No.: 10/742,020

(22) Filed: Dec. 19, 2003

(65) Prior Publication Data

US 2004/0267304 A1   Dec. 30, 2004

Related U.S. Application Data

(60) Provisional application No. 60/483,805, filed on Jun. 30, 2003.

(51) Int. Cl.
*A61B 17/00* (2006.01)

(52) U.S. Cl. .................................. 606/207; 606/99

(58) Field of Classification Search ............... 606/205, 606/206, 99, 100, 86, 107; 623/13.12, 14.12, 623/16.11–17.16
See application file for complete search history.

(56) References Cited

U.S. PATENT DOCUMENTS

| | | | |
|---|---|---|---|
| 4,791,924 A * | 12/1988 | Kelman | 606/107 |
| 4,873,976 A | 10/1989 | Schreiber | |
| 4,880,429 A | 11/1989 | Stone | |
| 5,007,934 A | 4/1991 | Stone et al. | |
| 5,108,421 A | 4/1992 | Fowler | |
| 5,108,438 A | 4/1992 | Stone | |
| 5,290,310 A | 3/1994 | Najiwerm et al. | |
| 5,306,311 A | 4/1994 | Stone et al. | |
| 5,318,589 A * | 6/1994 | Lichtman | 606/205 |
| 5,320,633 A | 6/1994 | Allen et al. | |
| 5,320,639 A | 6/1994 | Rudnick | |
| 5,374,268 A | 12/1994 | Sander | |
| 5,569,252 A | 10/1996 | Justin et al. | |

(Continued)

OTHER PUBLICATIONS

O'Connor's Textbook of Arthroscopic Surgery, $2^{nd}$ ed., 1992, Chapter 19.

*Primary Examiner*—Todd E Manahan
*Assistant Examiner*—Michael G. Mendoza

(57) ABSTRACT

A surgical instrument has a main shaft underlying a slide member. The slide member is movable in a proximal-distal direction. The distal end of the slide member has an open position and a closed position. The closed position is spaced from the open position in the proximal-distal direction. There is a gap between the distal end of the slide member and the distal end of the main shaft when the instrument is in the open position. The gap is smaller when the instrument is in the closed position. An implant can be received in the gap and delivered to a damaged tissue site using the instrument. An implant protector can be used when delivering the implant with the instrument. A pivotable implant cover can be used to protect the implant instead of the slide member.

6 Claims, 17 Drawing Sheets

U.S. PATENT DOCUMENTS

| | | | |
|---|---|---|---|
| 5,681,353 A | 10/1997 | Li et al. | |
| 5,693,069 A * | 12/1997 | Shallman | 606/205 |
| 5,702,462 A | 12/1997 | Oberlander | |
| 5,735,903 A | 4/1998 | Li et al. | |
| 5,951,587 A | 9/1999 | Qureshi et al. | |
| 5,980,524 A | 11/1999 | Justin et al. | |
| 5,993,475 A | 11/1999 | Lin et al. | |
| 6,042,610 A | 3/2000 | Li et al. | |
| 6,056,778 A | 5/2000 | Grafton et al. | |
| 6,152,935 A | 11/2000 | Kammerer et al. | |
| 6,156,044 A | 12/2000 | Kammerer et al. | |
| 6,293,961 B2 | 9/2001 | Schwartz et al. | |
| 6,306,156 B1 | 10/2001 | Clark | |
| 6,306,159 B1 | 10/2001 | Schwartz et al. | |
| 6,319,271 B1 | 11/2001 | Schwartz et al. | |
| 6,350,274 B1 | 2/2002 | Li | |
| 7,060,077 B2 | 6/2006 | Gordon et al. | |

* cited by examiner

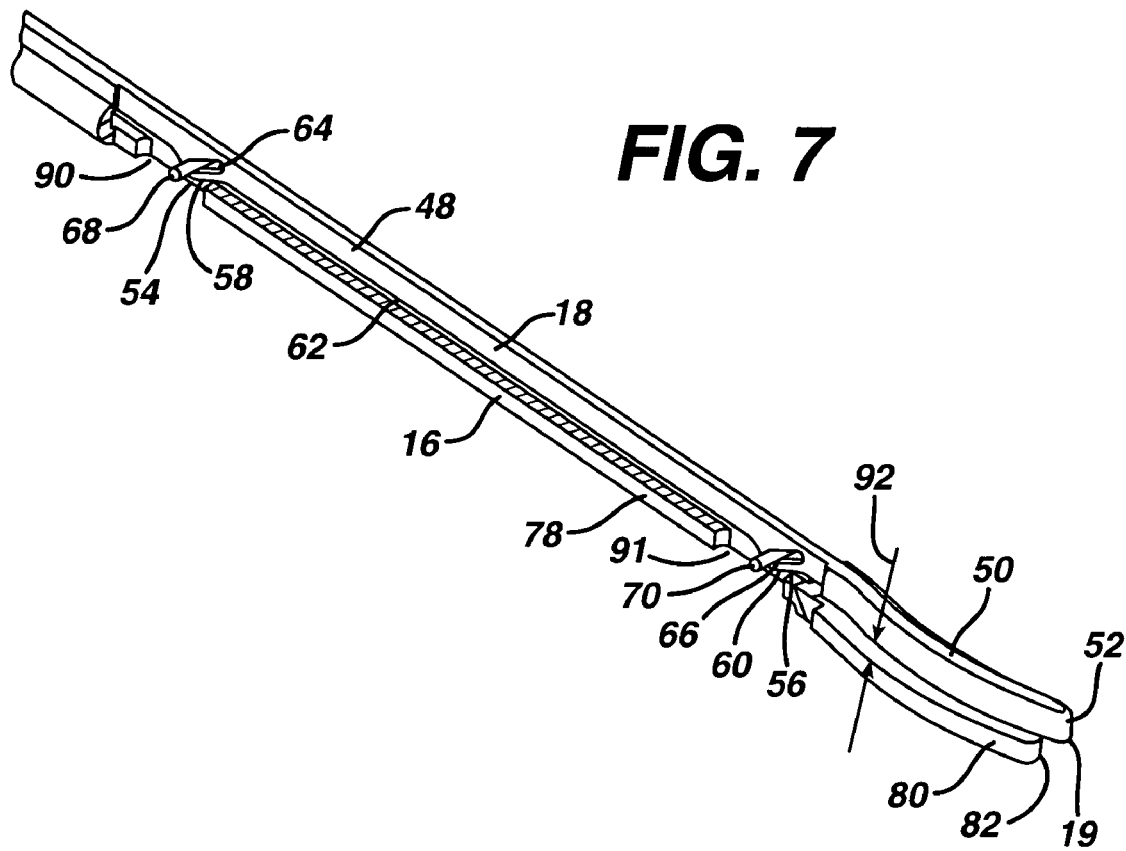
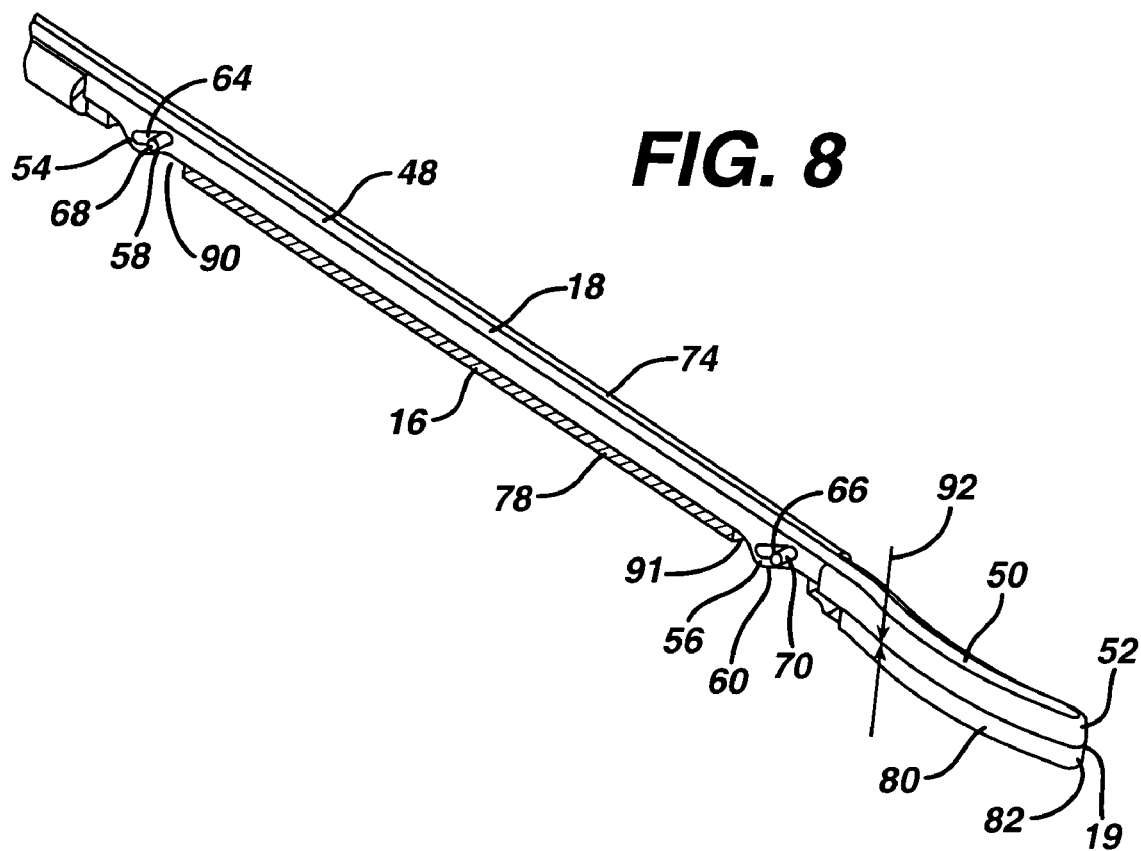

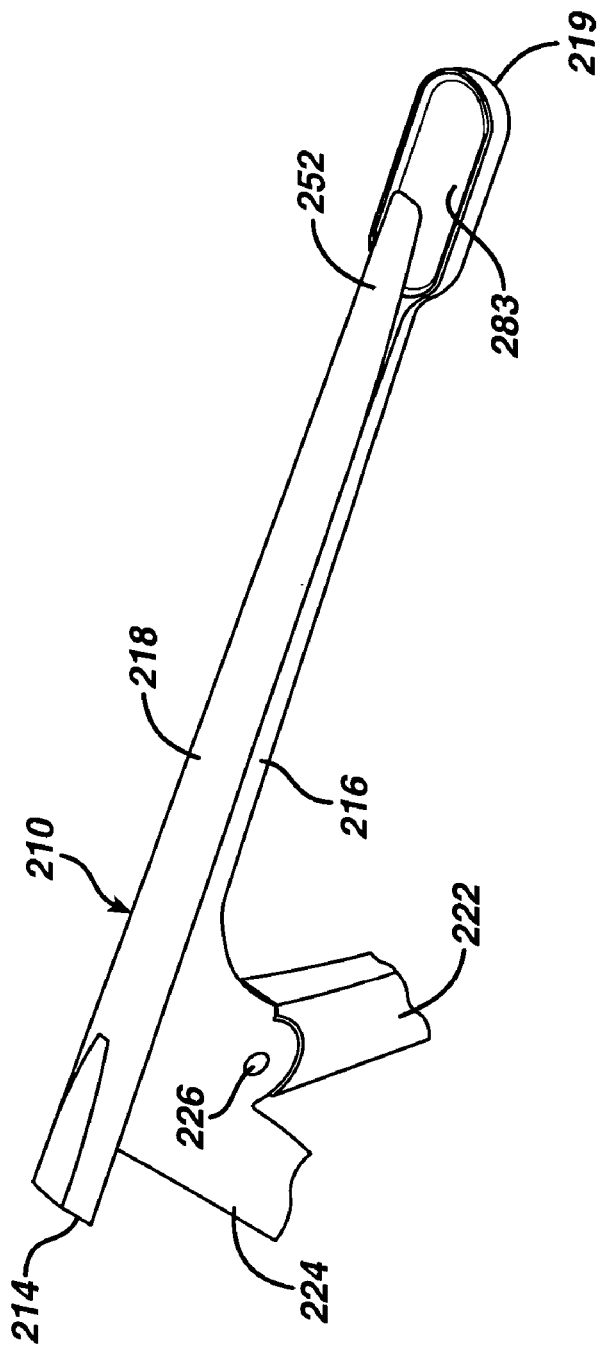
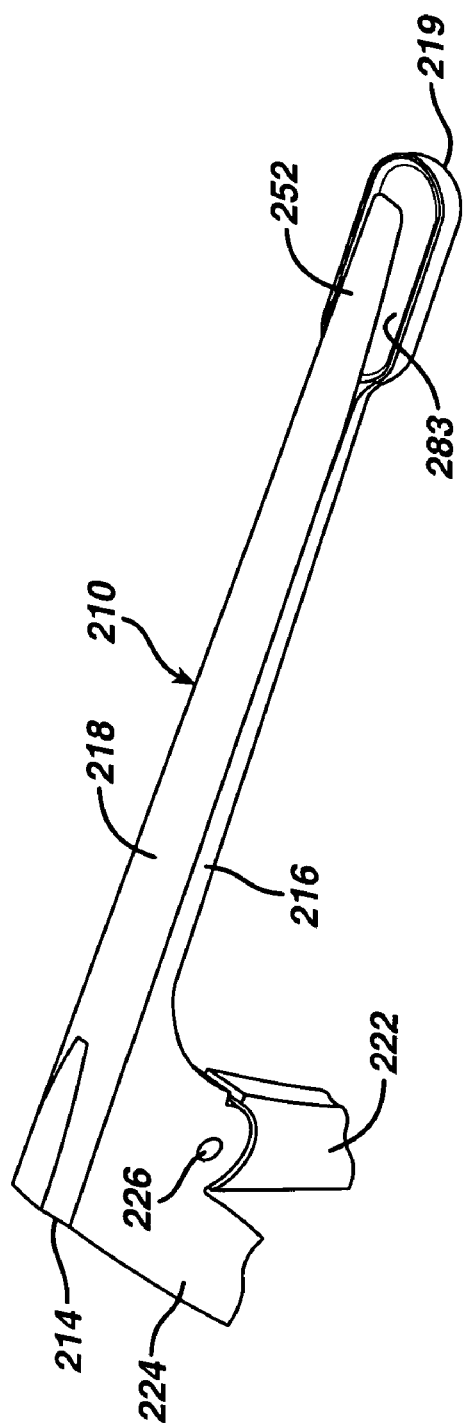
FIG. 25
FIG. 26

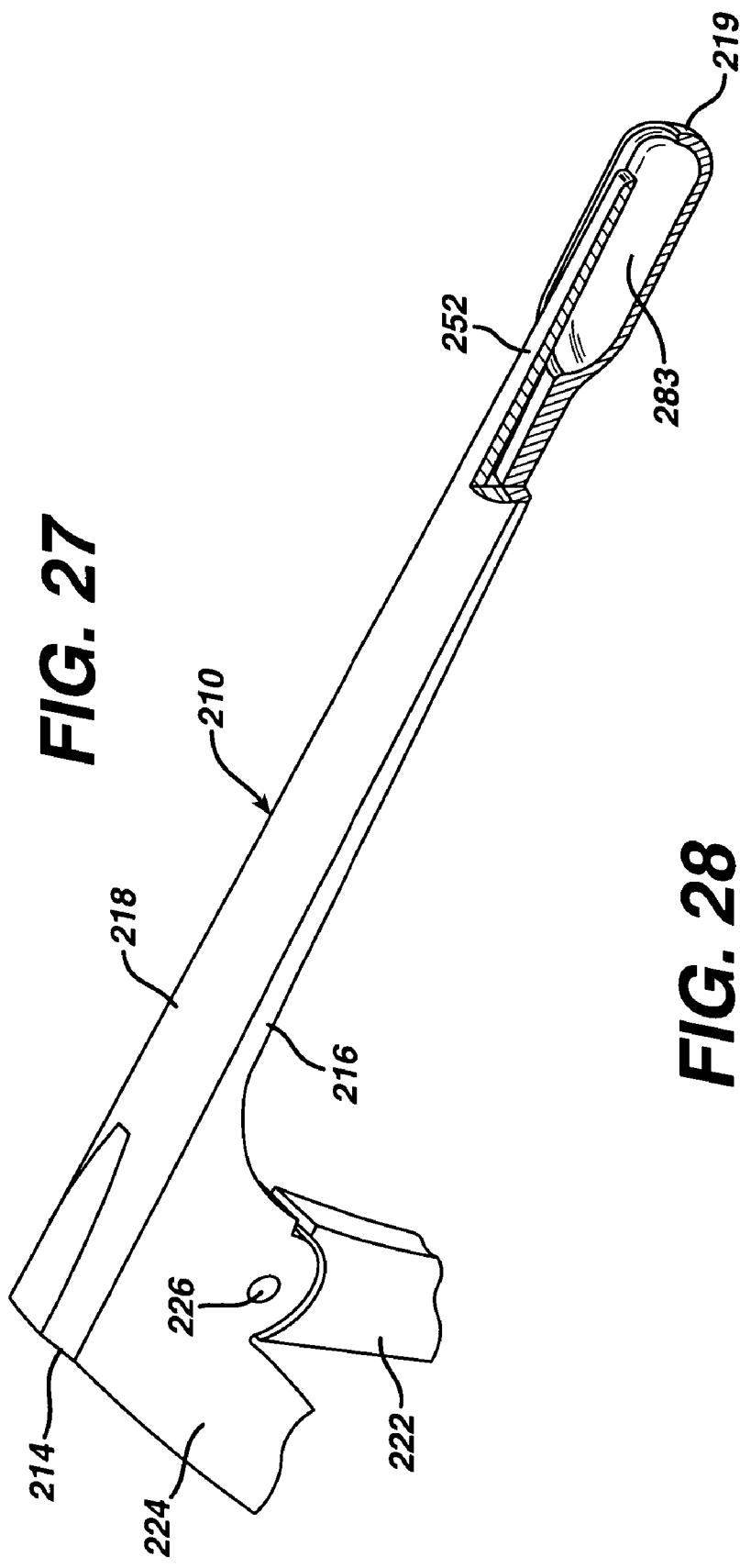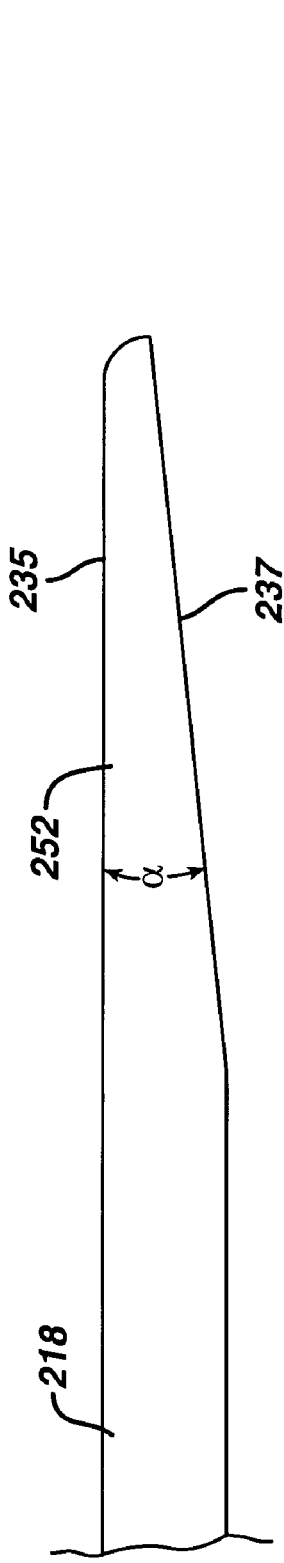

INSTRUMENT FOR DELIVERY OF IMPLANT

CROSS REFERENCE TO U.S. PROVISIONAL PATENT APPLICATION

This application is a Utility Application based upon a U.S. Provisional Patent Application Ser. No. 60/483,805 entitled "INSTRUMENT FOR DELIVERY OF IMPLANT" filed by Anthony D. Zannis, John W. Kemppainen, Andrew M. Jacobs, Carolyn K. Day, Rhonda B. Clarke, Herbert E. Schwartz, Prasanna Malaviya and Danny E. McAdams filed on Jun. 30, 2003, the complete disclosure of which is incorporated by reference herein.

FIELD OF THE INVENTION

The present invention relates generally to a surgical instrument for delivering an implant to a damaged tissue site in the human body.

BACKGROUND OF THE INVENTION

Several different types of soft tissue are found in human joints. For example, a joint can include articular hyaline cartilage, intra-articular fibrocartilage, tendons and ligaments. Articular hyaline cartilage is found on the surfaces of the bones of the joint. Intra-articular cartilage is found between the joint surfaces. Tendons connect muscle to the bones of the joint, and ligaments connect articular extremities of the bones of the joint.

When the soft tissue of a joint is no longer healthy, there can be debilitating pain in the joint. Soft tissue health can be adversely affected by disease, aging, or trauma. The adverse effects of disease, aging and trauma can be, for example, in the form of a tear in the soft tissue, or in the form of a breakdown, thinning or delamination of the tissue.

One form of intra-articular cartilage that is frequently damaged or degenerated is the meniscus of the knee. The meniscus is frequently damaged in twisting injuries. It is also damaged with repetitive impact over time. Meniscus degeneration can also occur by aging; as a person ages, the meniscus can become soft in places, so that even common motions like squatting can cause meniscal tears.

Common surgical procedures for treating meniscal damage include tear repairs and menisectomies. A tear repair is most commonly performed when the tear is a clean longitudinal vertical lesion in the vascular red zone of the meniscus. The basic strategy is to stabilize the tear by limiting or eliminating radial separation of the faces of the tear when the meniscus is load bearing. Many devices and surgical procedures exist for repairing meniscal tears by approximating the faces of the meniscus at the tear. Examples of such devices and procedures are disclosed in the following U.S. Pat. Nos.: 6,319,271; 6,306,159; 6,306,156; 6,293,961; 6,156,044; 6,152,935; 6,056,778; 5,993,475; 5,980,524; 5,702,462; 5,569,252; 5,374,268; 5,320,633; and 4,873,976.

Menisectomies involve the surgical removal of part of the meniscus. Such procedures have generally been performed in cases of radial tears, horizontal tears, vertical longitudinal tears outside the vascular zone, complex tears, or defibrillation. Although menisectomies provide immediate relief to the patient, in the long term the absence of part of the meniscus can cause cartilage wear on the condylar surface, eventually leading to arthritic conditions in the joint.

Such surgical procedures are commonly performed arthroscopically. In arthroscopy, small incisions are made at the affected joint to form portals for the insertion of instruments, including a small lens and lighting system (an arthroscope). The arthroscope is connected to a viewing device, such as a television monitor to allow the surgeon to see the interior of the joint. Other instruments are inserted through other portals to perform a variety of tasks. For example, the surgical instrument may include an implement for manipulating native tissue (for example, tissue grasping, tissue cutting, bone abrading).

Typical surgical instruments used in arthroscopic procedures include rongeurs, such as the Kerrison rongeur, punch forceps, basket forceps, suction punches and cup curet, for example. Examples of arthroscopic instruments are described and illustrated in O'Connor's Textbook of Arthroscopic Surgery, $2^{nd}$ ed., 1992, Chapter 19.

Other common surgical techniques in orthopaedic surgery include open surgery and mini-arthrotomy. For example, for knee surgery, the surgery may be performed by an open knee arthrotomy, where the incision may typically be 20-30 cm in length, and wherein the patella is everted during surgery. Knee surgery may also be performed by a mini-knee arthrotomy, where the incision is typically 10-13 cm in length and patella tension is avoided.

Intra-articular fibrocartilage is also present, for example, in the temporomandibular joint and between vertebrae. Injury and degeneration can also occur to the intra-articular fibrocartilage in these other joints.

Another common site of soft tissue injury and degeneration is the rotator cuff in the shoulder. The rotator cuff comprises the tendons that attach muscles to a bone in the shoulder. Where one of the tendons is thin, delaminated or frayed to the point that surgical repair or reconstruction is necessary, the damaged tendon can be reinforced with graft tissue or with an orthopaedic implant.

A variety of orthopaedic implants are available for treating damaged soft tissue at a joint site. One commercially available orthopaedic implant is the RESTORE orthobiologic implant. The RESTORE orthobiologic implant comprises layers of small intestine submucosa. The commercial RESTORE product is typically sold in the form of a thin circular sheet with a diameter of about 2.5 inches in diameter. Other shapes and sizes of RESTORE orthobiologic implants can be used. In addition, the surgeon can cut the commercial RESTORE product intra-operatively to the desired shape and size. The RESTORE implant is used in treating rotator cuff injuries.

Orthopaedic implants for treatment of damaged menisci are disclosed in the following U.S. Pat. Nos.: 6,042,610; 5,735,903; 5,681,353; 5,306,311; 5,108,438; 5,007,934; and 4,880,429.

SUMMARY OF THE INVENTION

Orthopaedic implants useful in approximating, repair or regeneration of fibrocartilage are disclosed in the following applications for U.S. patent application Ser. No. 10/195,794 entitled "Meniscus Regeneration Device and Method"; Ser. No. 10/195,719 entitled "Devices from Naturally Occurring Biologically Derived Materials"; Ser. No. 10/195,347 entitled "Cartilage Repair Apparatus and Method"; Ser. No. 10/195,344 entitled "Unitary Surgical Device and Method"; Ser. No. 10/195,341 entitled "Hybrid Biologic/Synthetic Porous Extracellular Matrix Scaffolds"; Ser. No. 10/195,606 entitled "Cartilage Repair and Regeneration Device and Method"; Ser. No. 10/195,354 entitled "Porous Extracellular Matrix Scaffold and Method"; Ser. No. 10/195,334 entitled "Cartilage Repair and Regeneration Scaffolds and Method"; Ser. No. 10/195,633 entitled "Porous Delivery Scaffold and Method", each of which is assigned to the same assignee as the present application, each of which was filed on Jul. 15, 2002, and each of which is hereby incorporated by reference herein. Cross reference is also made to U.S. patent application Ser. No. 10/172,347 entitled "Hybrid Biologic-Synthetic Bioabsorbable Scaffolds" which was filed on Jun. 14, 2002, which is assigned to the same assignee as the present application, and which is incorporated by reference herein. Additional orthopaedic implants are disclosed in U.S. Pat. No. 6,176,880, entitled "Tissue Grant Construct for Replacement of Cartilaginous Structures" and U.S. patent application Ser. Nos. 09/767,345 and 09/767,346 of the same title, both filed on Jan. 23, 2001 and claiming priority to U.S. Pat. No. 6,176,880, which are incorporated by reference herein.

As used herein "implant" is intended to mean any device that is intended to be implanted at a damaged tissue site for the approximation, repair or regeneration of tissue at the damaged tissue site. "Orthopaedic implant" is intended to mean any device that is intended to be implanted at a joint site for the approximation, repair or regeneration of soft tissue at the joint site. While "implant" and "orthopaedic implant" are intended to include all of the devices identified in the preceding paragraph and commercial devices such as the RESTORE™ orthobiologic implant, "implant" and "orthopaedic implant" should not be limited to these particular devices or to any particular material unless expressly set forth in the claims. For example, "implant" and "orthopaedic implant" as used herein are intended to include devices made from synthetic sources, from purified natural fibers as well as devices made from naturally occurring tissue. An implant may comprise a tissue scaffold, patch or graft (including autografts, allografts and hetergrafts), for example. In addition, "implant" and "orthopaedic implant" are intended to include such devices either alone or in combination with bioactive agents, biologically-derived agents, cells, a biological lubricant, a biocompatible synthetic or a biocompatible inorganic material, for example.

Materials forming orthopaedic implants can find use in other parts of the body as well. Accordingly, the term "implant" is intended to mean such materials regardless of their intended end use.

The present invention provides a surgical instrument that allow for delivery of implants to a damaged tissue site. The damaged tissue site can be a damaged joint site, such as in the area of the meniscus in the human knee joint or in the area of the rotator cuff of the shoulder joint, and the implant can be an orthopaedic implant used to approximate, repair or regenerate damaged or diseased soft tissue at the damaged joint site.

In one aspect, the present invention provides a surgical instrument for delivering an implant to a damaged tissue site. The surgical instrument comprises a main shaft and a slide member. The main shaft has a proximal end and a distal end. The side member is juxtaposed with the main shaft and also has a proximal end and a distal end. The surgical instrument has open and closed positions. The slide member is movable in a proximal-distal direction with respect to the main shaft to move the surgical instrument between the open and closed positions. The distal end of the slide member has an open position when the surgical instrument is in the open position and a closed position when the surgical instrument is in the closed position. The closed position of the distal end of the slide member is spaced from the open position of the distal end of the slide member in the proximal-distal direction. There is a gap between the distal end of the slide member and the distal end of the main shaft when the instrument is in the open position. There is a smaller gap between the distal end of the slide member and the distal end of the main shaft when the instrument is in the closed position.

In another aspect, the present invention provides a surgical instrument for delivering an implant to a damaged tissue site. The surgical instrument comprises a main shaft and a cover. The main shaft has a distal end shaped to define a well for receiving a substantial portion of the implant. The cover is movable between a position substantially overlying the well to protect the implant to another position wherein a substantial part of the well is exposed.

In another aspect, the present invention provides a combination comprising a surgical instrument for delivering an implant to a damaged tissue site and an implant. The implant includes an edge. The surgical instrument includes a main shaft having a distal end and a slide member juxtaposed with the main shaft. The slide member has a distal end. The edge of the implant is received between the distal end of the main shaft and the distal end of the slide member. The shape of the distal end of the main shaft and the shape of the distal end of the slide member follow the shape of the edge of the implant.

BRIEF DESCRIPTION OF THE DRAWINGS

The invention will be better understood by reference to the figures of the drawings wherein like numbers denote like parts throughout and wherein:

FIG. 7 is a perspective view of a portion of the main shaft and slide rod of the instrument of FIGS. 1-6, with part of the main shaft removed for purposes of illustration and showing the instrument in the open or unclamped position;

FIG. 8 is a perspective view of a portion of the main shaft and slide rod of the instrument of FIGS. 1-6, with part of the main shaft removed for purposes of illustration and showing the instrument in the closed or clamped position;

FIG. 25 is a perspective view of the instrument of FIG. 24, with parts of the handle removed;

FIG. 26 is a perspective view of the instrument of FIG. 24, similar to FIG. 25 but with the instrument in the closed or clamped position;

FIG. 27 is a perspective view of the instrument of FIG. 24, similar to FIG. 26 but with parts of the instrument shown in cross-section;

FIG. 28 is a side elevation of the distal end of the slide arm of the instrument of FIG. 24;

DETAILED DESCRIPTION OF THE ILLUSTRATED EMBODIMENTS

Figure 1:
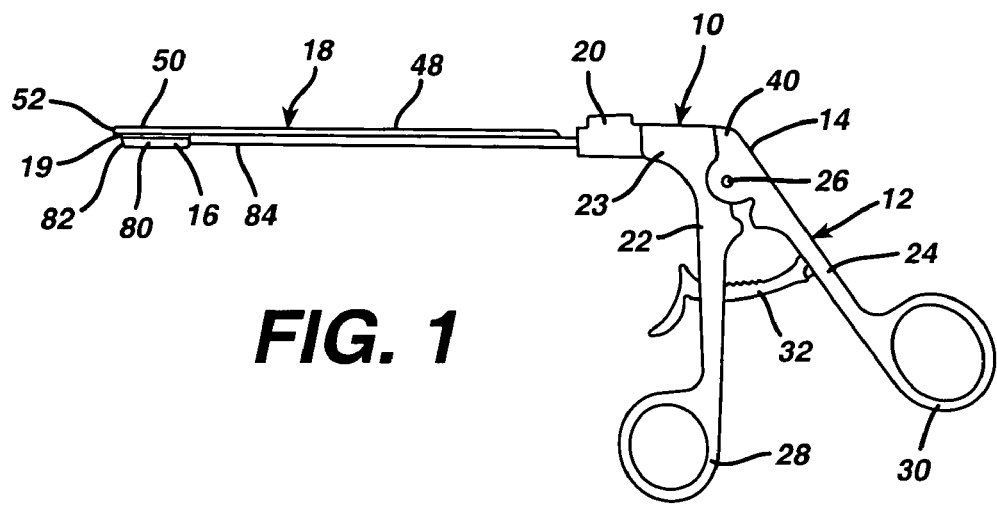
FIG. 1 is a side elevation of a first embodiment of a surgical instrument illustrating the features of the present invention, showing the instrument in an open or unclamped position.

The instrument of the present invention is useful in delivering an orthopaedic implant, as defined above, to a damaged joint site in the body. The damaged joint site may for example be an intra-articular site such as the knee, where the instrument can be used to deliver an orthopaedic implant for use in approximating, repairing or regenerating a diseased or damaged meniscus. The damaged intra-articular site may be in other locations in the body, such as the temporomandibular joint, between vertebrae, or any site where there is fibrocartilage in need of approximation, repair or regeneration. The instrument of the present invention can also be used to deliver an orthopaedic implant to location outside of the intra-articular space of a joint site. For example, the instrument of the present invention can be used to deliver an orthopaedic implant to a damaged joint site such as the area of the rotator cuff of the shoulder joint site. Unless expressly limited in the claims, "joint site" as used herein is intended to include the intra-articular space and other areas near the bones comprising a joint. "Damaged joint site", unless expressly limited in the claims, is intended to mean such a joint site that requires surgical repair, whether due to injury, degeneration or disease.

The instrument of the present invention may also find utility in delivering an implant to damaged tissue sites other than the joints. "Damaged tissue site", unless expressly limited in the claims, is intended to mean a tissue site that requires surgical repair, whether due to injury, degeneration or disease.

Several embodiments of the instrument of the present invention are illustrated in the accompanying drawings. The first embodiment of the instrument is illustrated in FIGS. 1-18 and 21-22. The first illustrated instrument 10 includes a handle 12 at the proximal end 14, a main shaft 16 and a slide rod 18. The main shaft 16 and slide rod 18 extend from the handle 12 to the distal end 19 of the instrument 10. The first illustrated instrument 10 may also optionally include a delivery guide 20, shown in FIGS. 1, 3, 21 and 22 but not in FIGS. 2, 4 and 5-20.

The handle 12 of the first illustrated instrument 10 includes two arms 22, 24 connected together at a pivot 26. Each arm 22, 24 includes a grip portion 28, 30 through which the surgeon may insert a thumb and a finger and squeeze to pivot the arms about pivot 26. As the grip portions 28, 30 are brought closer together, the slide arm 18 is moved from the open or unclamped position shown in FIGS. 1-2, 5 and 7 to the closed or clamped position shown in FIGS. 3-4, 6 and 8. FIGS. 1 and 3 also illustrate a possible locking mechanism 32 that cooperates with the arms 22, 24 for locking the slide arm 18 in either the open or closed positions.

Figure 12:
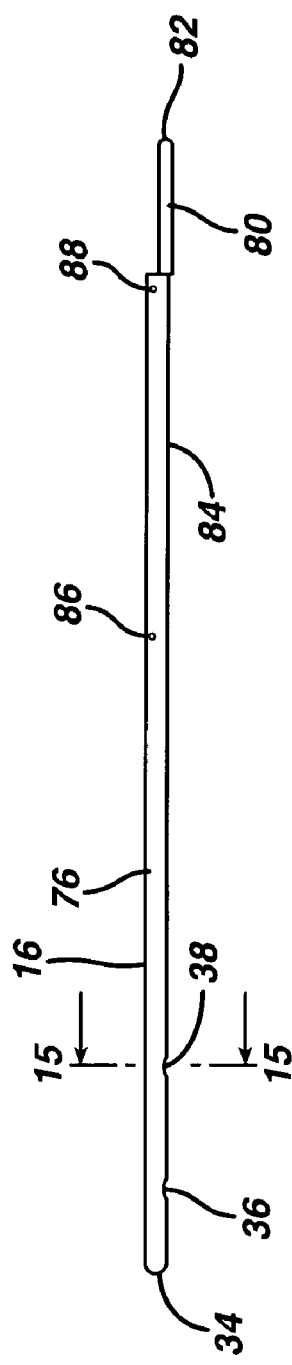
FIG. 12 is a side elevation of the main shaft of FIG. 11.

One arm 22 has a body portion 23 that is connected to a proximal end 34 of the main shaft 16 of the instrument 10 through standard means, such as a set screw or the like. The body portion 23 of the arm 22 is opposite the grip portion 28 and has an opening and channel (not shown) extending in a proximal-distal direction to receive the proximal end portion 34 of the main shaft 16. As shown in FIG. 12, the proximal end portion 34 of the main shaft 16 may have indentations or cavities 36, 38 that align with holes (not shown) in the body portion 23 of the arm 22 so that screws or the like can be used to secure the main shaft 16 to the body 23 of the arm 22. It will be appreciated that other means of connecting the main shaft 16 to the arm 22 may be used, and that the main shaft 16 and arm 22 could be made integral if desired.

The other arm 24 has a top end 40 opposite its grip portion 30. The pivot 26 that connects the two arms 22, 24 is positioned between the top end 40 and grip portion 30. When the grip portions 28, 30 are squeezed together, the top portion 40 of the arm 24 is pivoted in a generally proximal direction. When the grip portions 28, 30 are released, the top end 40 of the arm 24 is pivoted in a generally distal direction.

Figure 10:
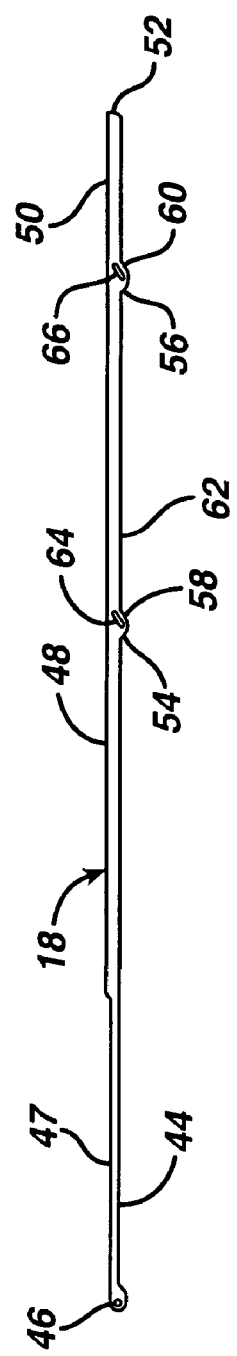
FIG. 10 is a side elevation of the slide rod of FIG. 9.

The top end 40 of the arm 24 has a hole or slot 42 (see FIGS. 5-6) that receives the proximal end 44 of the slide rod 18. A pin 45 or other suitable mechanical connector is used to connect the slide rod 18 to the top end 40 of the arm; this pin may provide a pivotable connection. As shown in FIG. 10, the proximal end 44 of the slide rod 18 has a hole 46 to receive the pin 45. A portion of the slide rod 18 at its proximal end 44 has a reduced height or thickness; this portion, designated 47 in FIG. 10, extends through the channel (not shown) in the body 23 of arm 22. Thus, when the top end 40 of the arm 24 is moved in a distal direction, the slide rod 18 is also moved in a distal direction; when the top end 40 of the arm 24 is moved in a proximal direction, the side rod 18 is also moved in a proximal direction.

Figure 9:
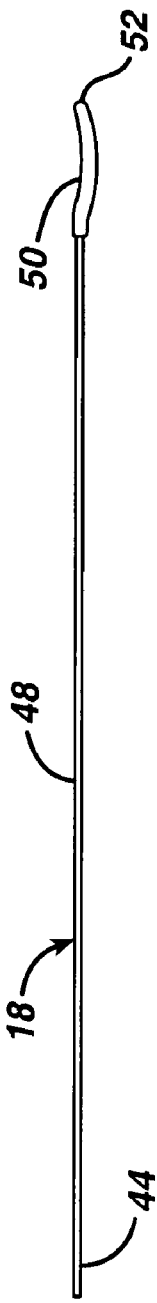
FIG. 9 is a top plan view of the slide rod of the instrument of FIGS. 1-8.

As shown in the top plan view of FIG. 9, the slide rod 18 has a thin elongate portion 48 extending from its proximal end 44 to a thicker curved portion 50 at its distal end 52. As shown in the side elevation view of FIG. 10, the slide rod also has a pair of spaced, integral downward-extending extensions 54, 56. Each extension 54, 56 has a distal edge or surface 58, 60 defining an obtuse angle with the bottom edge or surface 62 of the adjacent segments of the thin elongate portion 48. The distal edges 58, 60 are parallel to each other. Each extension 54, 56 also has a through slot 64, 66 (see FIGS. 7-8 and 10). The through slots 64, 66 of both extensions 54, 56 are parallel to each other and extend upward in a distal direction. As shown in FIGS. 7-8, the through slots 64, 66 each receive a pin 68, 70.

A substantial part of the thin elongate portion 48 of the slide rod 18 is received in an elongate channel 72 of the main shaft 16. The channel 72 is defined by two spaced parallel side walls 74, 76 and a bottom wall 78. The channel 72 extends from the junction of the main shaft 16 with the body 23 of the arm 22 to a thick curved portion 80 at the distal end 82 of the main shaft 16. As shown in FIG. 12, the curved portion 80 of the main shaft 16 is displaced downward from the bottom edge or surface 84 of the bottom wall 78.

Figure 11:
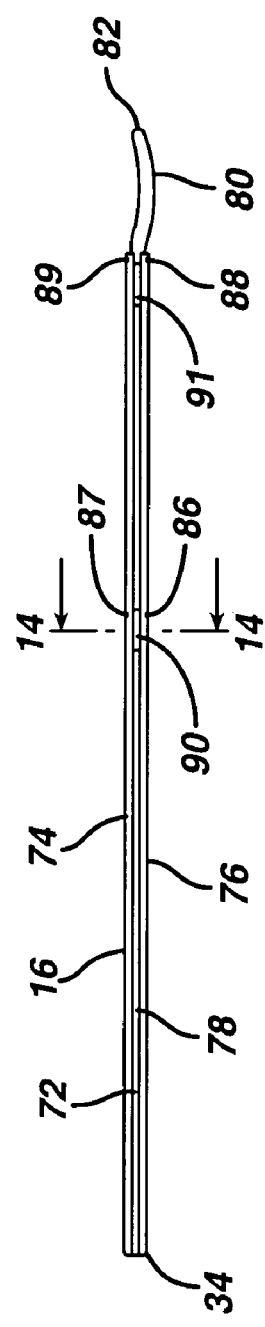
FIG. 11 is a top plan view of the main shaft of the instrument of FIGS. 1-8.

As shown in FIGS. 11-12, the side walls 74, 76 of the main shaft 16 have spaced, aligned through holes 86, 87, 88, 89. These through holes 86, 87, 88, 89 receive pins 68, 70 to mount the slide rod 18 to the main shaft 16. As shown in FIG. 11, the bottom wall 78 has a pair of slots 90, 91 positioned near the through holes 86, 87, 88, 89. As shown in FIGS. 7-8, the extensions 54, 56 of the slide rod 18 are received in these slots 90, 91.

As can be seen in FIGS. 5-8, the curved portions 50, 80 of the main shaft 16 and slide rod 18 are similarly shaped. Each has a radius of about 1.1 inches. In the illustrated embodiment, the curved portion 50 of the slide rod has a length of 0.773 inches and the curved portion 80 of the main shaft 16 has a length of 0.783 inches. It should be understood that these dimensions are provided as examples only; the present invention is not limited to any particular dimension unless expressly set forth in the claims.

Figure 2:
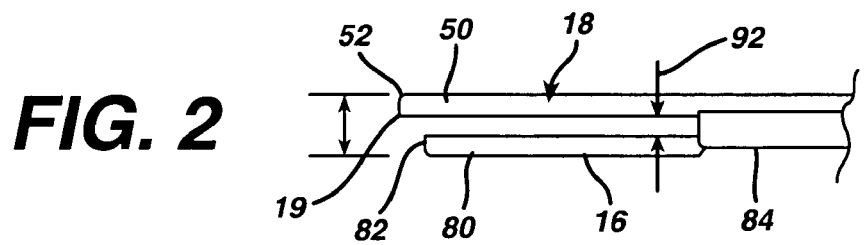
FIG. 2 is an enlarged view of the distal end of the instrument of FIG. 1.
Figure 3:
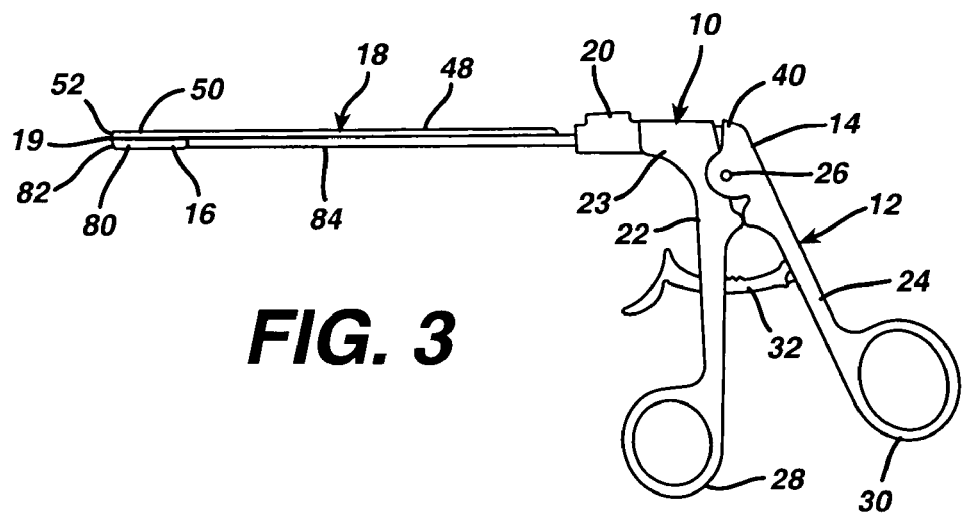
FIG. 3 is a side elevation of the instrument of FIGS. 1-2, showing the instrument in a closed or clamped position.
Figure 4:
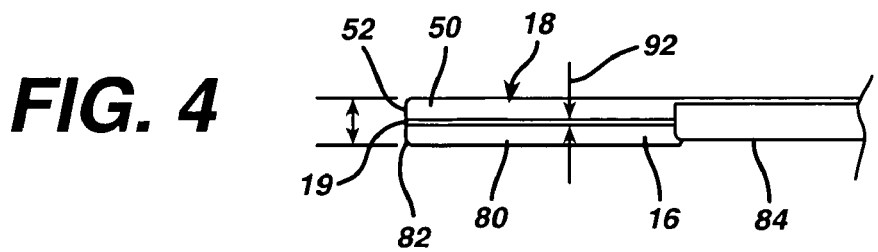
FIG. 4 is an enlarged view of the distal end of the instrument of FIGS. 1-3, shown in the closed or clamped position of FIG. 3.
Figure 5:
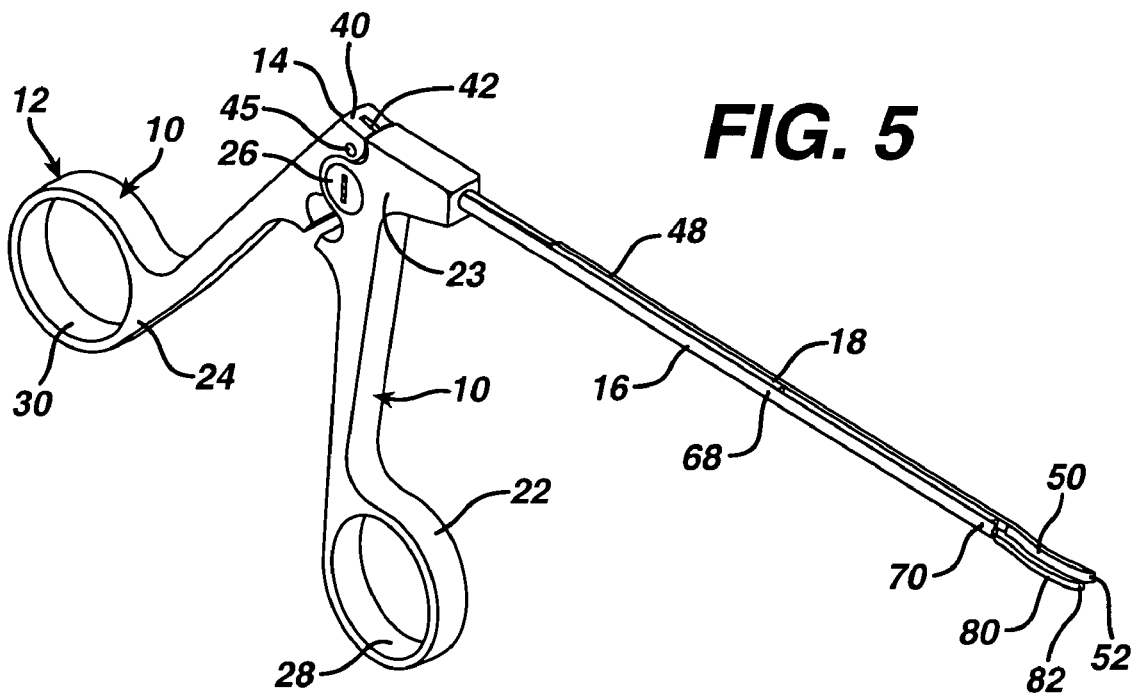
FIG. 5 is a perspective view of the instrument of FIGS. 1-4, shown in the open or unclamped position and with the delivery guide removed for purposes of illustration.
Figure 6:
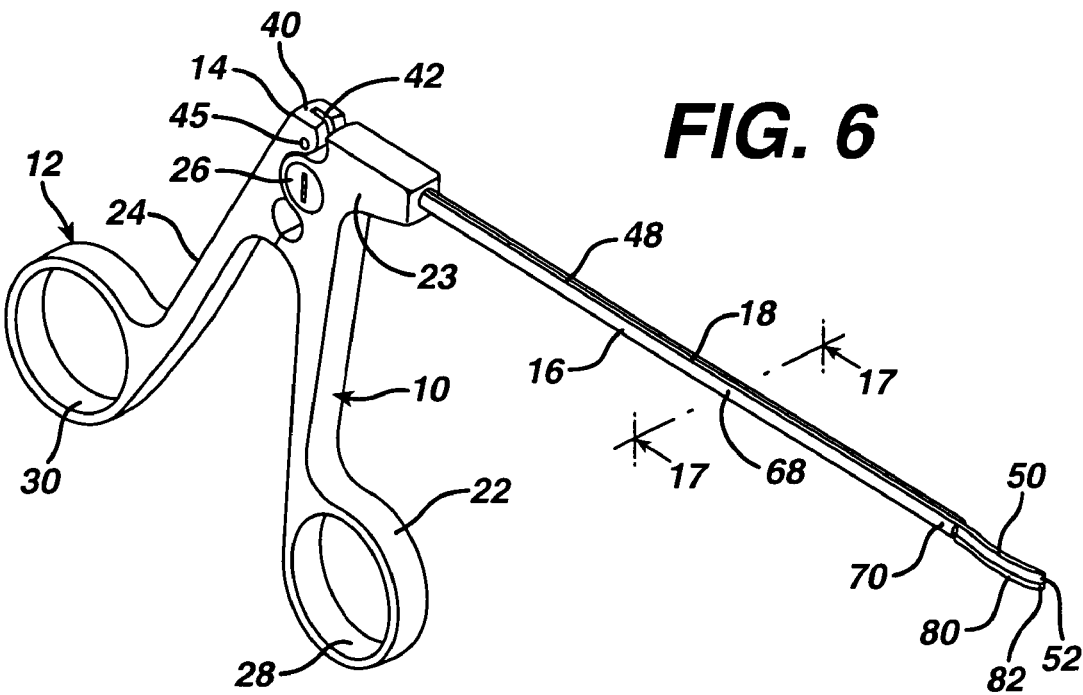
FIG. 6 is a perspective view of the instrument of FIGS. 1-5, shown in the closed or clamped position and with the delivery guide removed for purposes of illustration.

To use the first illustrated instrument 10, the grips 28, 30 are moved apart to place the instrument in the open or unclamped position shown in FIGS. 1-2, 5 and 7. In this position, the distal end 52 of the slide rod 18 extends distally beyond the distal end 82 of the main shaft 16. As shown in FIGS. 2 and 7, the curved portions 50, 80 of the slide rod 18 and main shaft 16 are spaced apart by a gap 92 of about 1-2 mm. The total height of the distal end of the instrument, including the heights of the gap 92 (at the fully open or unclamped position) and the heights of the curved portions 50, 80 is about 5 mm.

Figure 13:
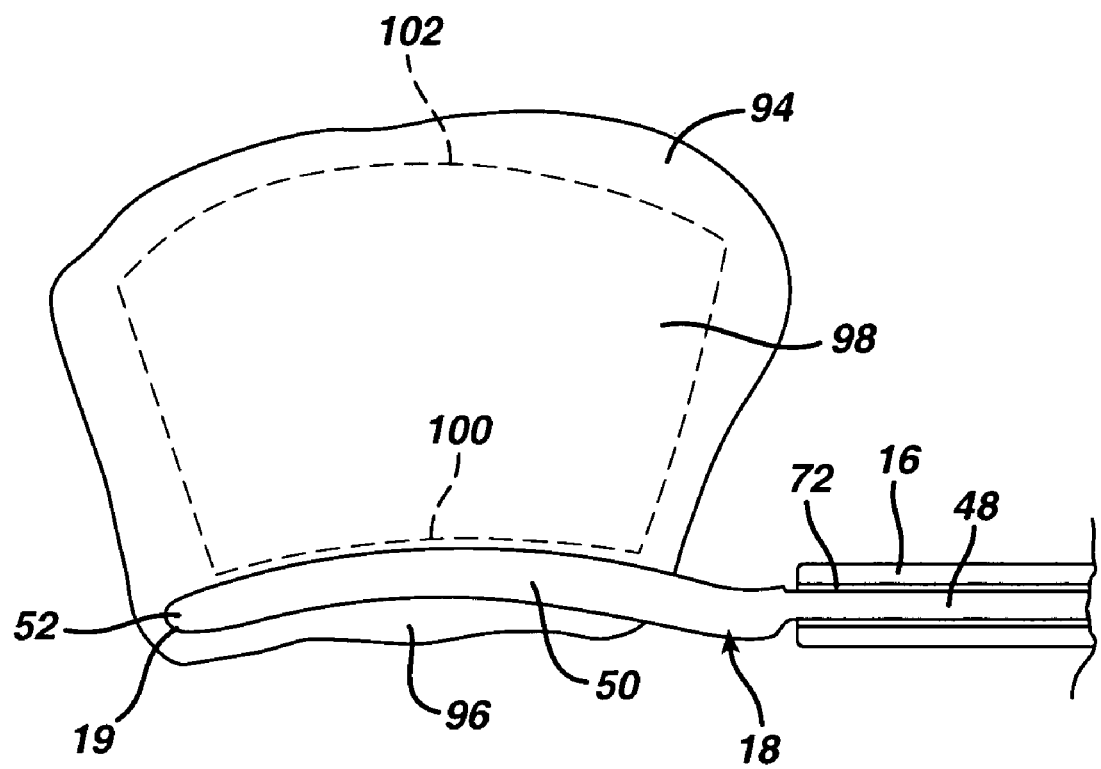
FIG. 13 is a top plan view of the distal end of the instrument of FIGS. 1-8 showing an orthopaedic implant held between the main shaft and the slide rod.
Figure 14:
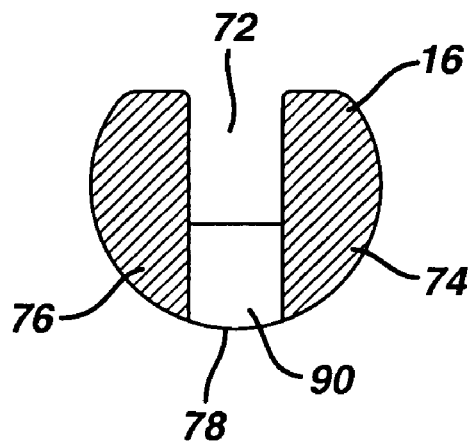
FIG. 14 is a transverse cross-section of the main shaft of the instrument of FIGS. 1-8, taken along line 14-14 of FIG. 11.
Figure 15:
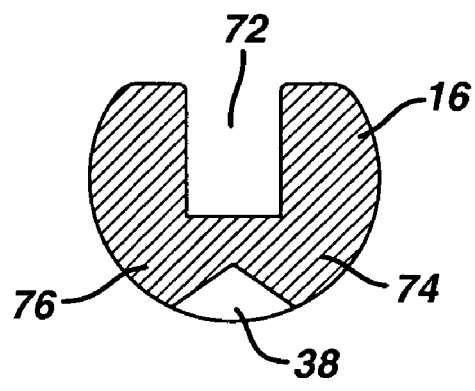
FIG. 15 is a transverse cross-section of the main shaft of the instrument of FIGS. 1-8, taken along line 15-15 of FIG. 12.
Figure 16:
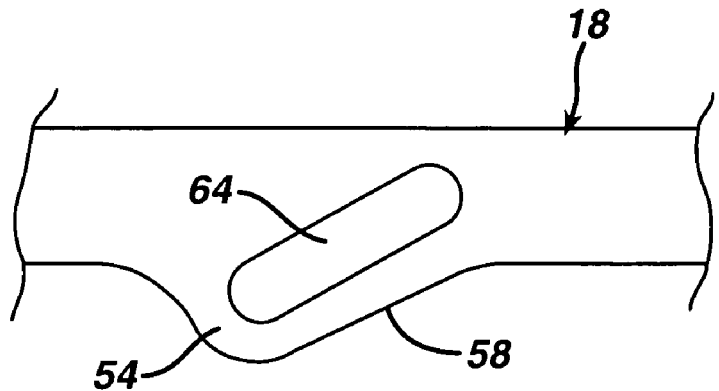
FIG. 16 is an enlarged side view or elevation of one of the extensions of the slide rod of FIGS. 9-10.
Figure 17:
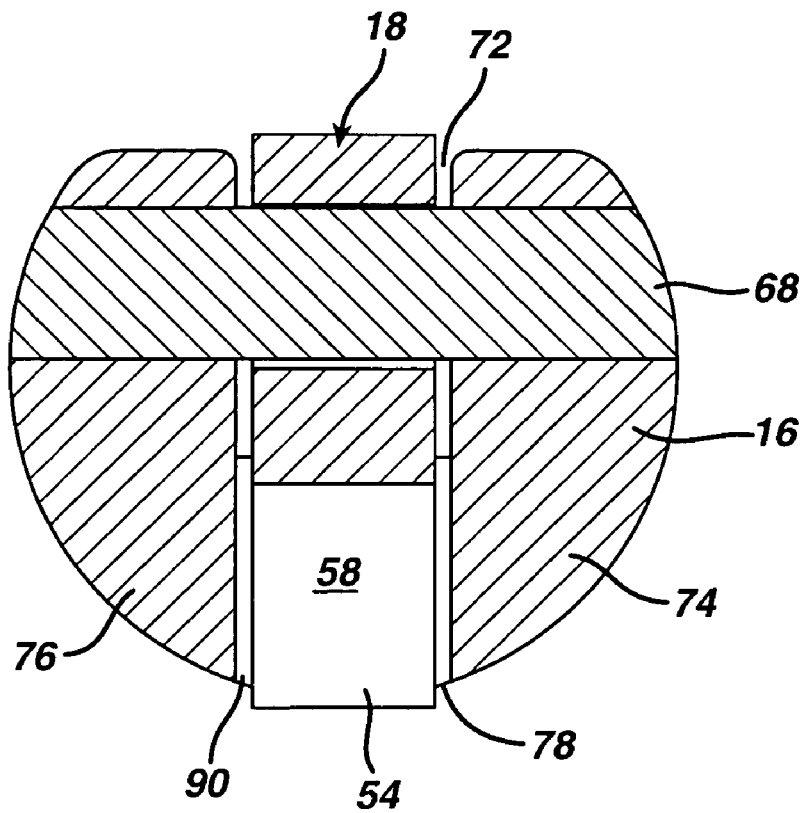
FIG. 17 is a transverse cross-section of the slide rod assembled on the main shaft, taken along line 17-17 of FIG. 6.

With the instrument in the open or unclamped position, the surgeon can then place a portion of the implant in the gap between the spaced curved portions 50, 80 of the slide rod 18 and main shaft 16. As shown in FIG. 13, a meniscal implant, shown at 94 may comprise a flat periphery 96 and an inner wedge-shaped portion 98 with curved inner and outer edges 100, 102. Such a meniscal implant 94 may be used to replace a part of a damaged meniscus removed in a menisectomy. In the illustrated embodiment, the curvature of the spaced curved portions 50, 80 of the slide rod 18 and main shaft 16 follows the curvature of the inner edge 100 of the wedge-shaped portion 98 of the implant. Thus, the curvature of the spaced portions 50, 80 of the slide rod and main shaft protect the inner edge 100 of the wedge-shaped portion 98 of the implant as it is introduced to the damaged tissue site.

The flat periphery 96 of the implant 94 is inserted in the gap 92 between the curved portions 50, 80 of the main shaft 16 and slide rod 18. The curved inner edge 100 of the inner wedge-shaped portion 98 of the implant is placed along side the curved edges of the portions 50, 80 of the main shaft and slide rod.

When the instrument is in this fully open or unclamped position, the pins 68, 70 are at the lowest ends of the slots 64, 66 in the slide rod 18, and the slide rod is slightly raised with respect to the channel 72 of the main shaft 16. As shown in FIG. 7, in this position, substantial portions of the slide rod extensions 54, 56 are above the slots 90, 91 and the distal end 52 of the slide rod 18 extends slightly beyond the distal end 82 of the main shaft 16.

Once the implant 94 is in position in the gap 92, the surgeon may close the instrument to clamp the implant between the curved portions 50, 80 of the main shaft 16 and slide rod 18. The surgeon moves the grip portions 28, 30 of the arms 22, 24 closer together, causing the top end 40 of the arm 24 to pivot away from the body 23 of the arm 22. As the top end 40 of the arm 24 moves away from the body 23 of arm 22, the slide rod 18 is pulled in a proximal direction. As the slide rod 18 moves proximally, it also moves deeper into the channel 72 as the slots 64, 66 of the extensions 54, 56 move downward along the pins 68, 70 until the pins 68, 70 are at or near the top ends of the slots 64, 66. As the slide rod 18 is moved proximally and deeper into the channel 72, the extensions 54, 56 move deeper into the slots 90, 91 of the main shaft 16, and the curved portion 50 of the slide rod 18 moves closer to the curved portion of the main shaft 80. As the two curved portions 50, 80 moves closer together, the gap 92 is closed, clamping the periphery 96 of the implant 94 between the two curved portions 50, 80. Thus, the total height of the distal end of the instrument decreases.

The surgeon may then deliver the implant 94 to the damaged tissue site. If the surgery is an arthroscopic procedure, or a mini-arthrotomy, access to the damaged tissue site may be confined. To prevent the implant 94 from being damaged by the close confines of the damaged tissue site, the surgeon may use the first illustrated instrument in combination with an implant protector.

Figure 18:
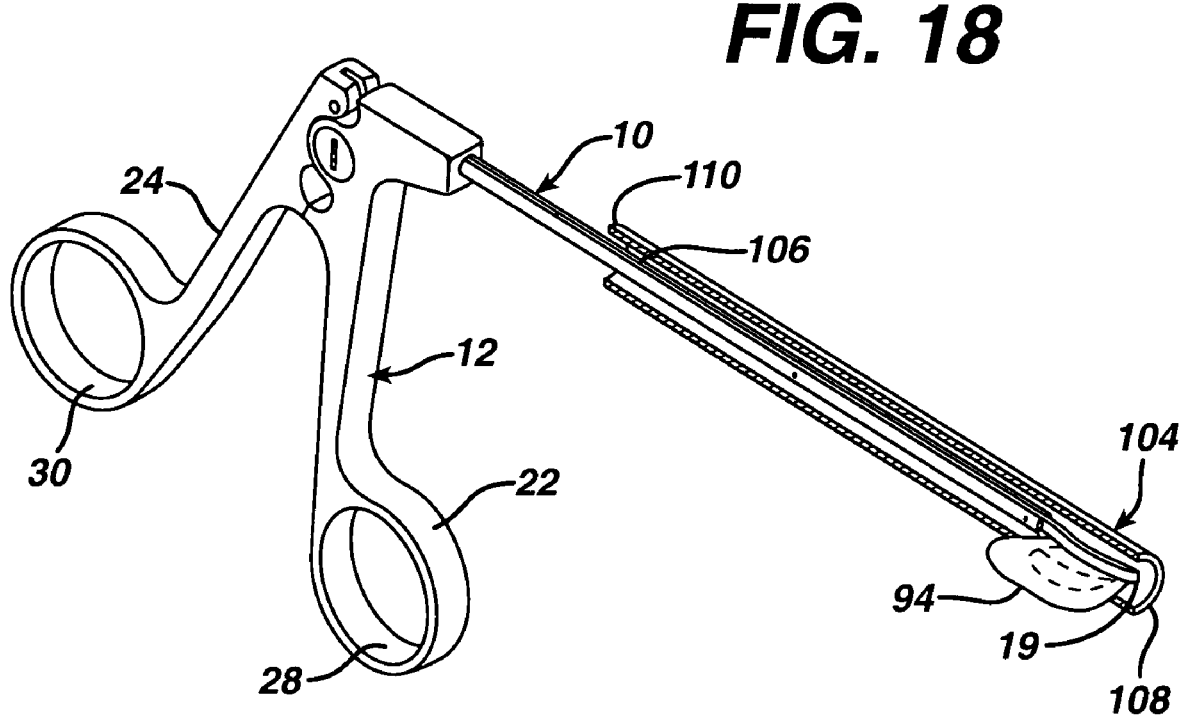
FIG. 18 is a perspective view of the instrument of FIGS. 1-6, shown in the closed or clamped position with an implant clamped at the distal end of the instrument, and shown in combination with an implant protector, the implant protector being shown in longitudinal cross-section.
Figure 19:
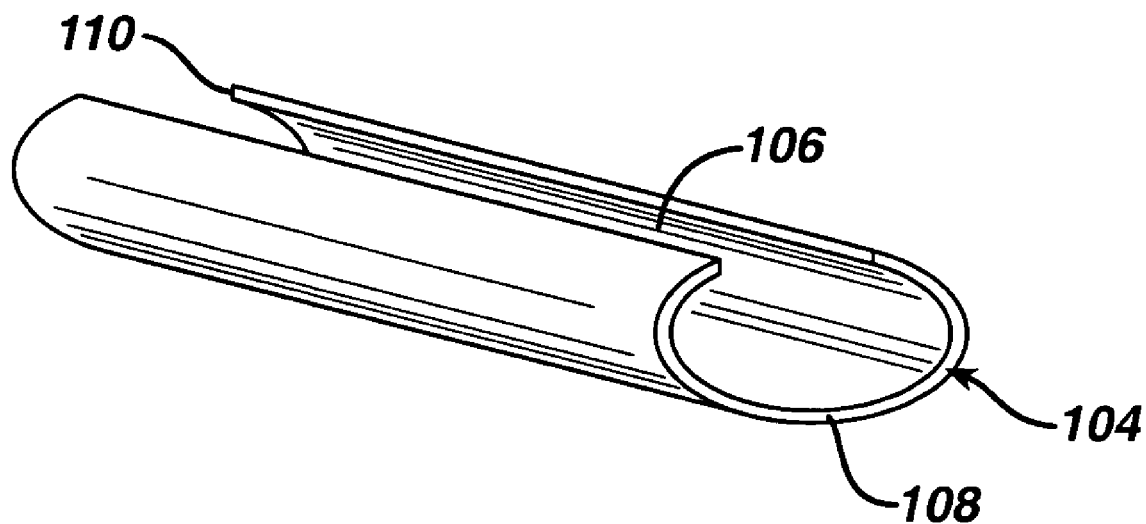
FIG. 19 is a perspective view of the implant protector of FIG. 18.

One form of implant protector that may be used is an elongate tube as illustrated in FIGS. 18-19. As there shown, the implant protector 104 comprises a hollow, open-ended tube that is oval-shaped in cross-section. The implant protector 104 has a slot 106 extending along its length. In the illustrated embodiment, the slot 106 is along the top of the tube. To use the instrument 10 with the implant protector 104, the surgeon may place the distal end 108 of the implant protector at the damaged tissue site, such as in the intra-articular space of the knee near the area where a portion of the meniscus has been removed. The implant protector 104 is long enough so that its proximal end 110 is exposed outside of the patient's body.

The surgeon may insert the distal end 19 of the instrument 10, with the implant 94 captured by the curved portions 50, 80, into the implant protector 104 and move the distal end 19 of the instrument 10 in a distal direction along the length of the implant protector 104 until the distal end 19 of the instrument 10 and the implant 94 are at the damaged tissue site beyond the distal end 108 of the implant protector 104. The surgeon may then release the implant 94 from the instrument 10.

To release the implant 94 from the instrument 10, the grip portions 28, 30 of the arms 22, 24 are moved apart. As the grip portions 28, 30 are moved apart, the slide rod 18 is moved in a distal direction. As the slide rod 18 moves distally, the extensions 54, 56 move upwardly and distally along the pins 68, 70 and the entire slide rod 18 moves upward in the channel 72. As the slide rod 18 moves in an upward and distal direction, the curved portion 50 of the slide rod separates from the curved portion 80 of the main shaft 16, releasing the implant 94. The released implant may then be moved into its final position and secured to native tissue.

The surgeon may also use the device disclosed in U.S. patent application Ser. No. 10/609,768 entitled "Implant Stabilizing Instrument, Kit and Method," filed concurrently herewith by Andrew M. Jacobs, Carolyn K. Day, Rhonda B. Clarke, Herbert E. Schwartz, John W. Kemppainen, Prasanna Malaviya and Anthony D. Zannis, which is incorporated by reference herein in its entirety. The instrument, kit and method disclosed in that patent application may be used to move and stabilize the implant while securing the implant to the native tissue.

It will be appreciated that the instrument 10 requires little space when in the open or unclamped position. This feature of the invention is particularly advantageous when delivering an implant to a damaged tissue site that is closely confined, such as in the intra-articular space of a joint.

To remove the instrument 10 from the implant protector 104, the instrument may be pulled in a proximal direction until its distal end 19 is free from the implant protector 104 outside of the patient's body. Alternatively, the surgeon may raise the instrument so that the main shaft 16 and slide rod 18 are raised through the slot 106 of the implant protector 104. Once the main shaft 16 and slide rod 18 are clear of the implant protector 104, the instrument may be moved out of the patient's body.

Figure 20:
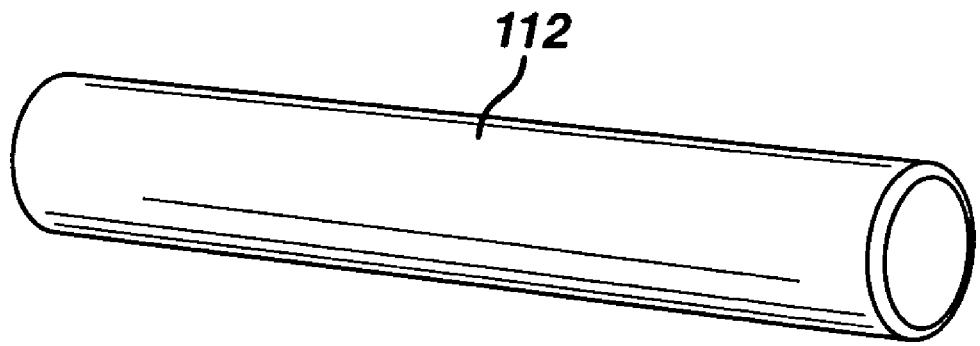
FIG. 20 is a perspective view of an alternate implant protector.

Alternative implant protectors can be used with the instrument 10. For example, as shown in FIG. 20, an implant protector 112 can comprise an elongate hollow, open-ended tube of circular cross-section. If desired, the implant protector 112 can have a slot as in the first illustrated implant protector 104.

Figure 21:
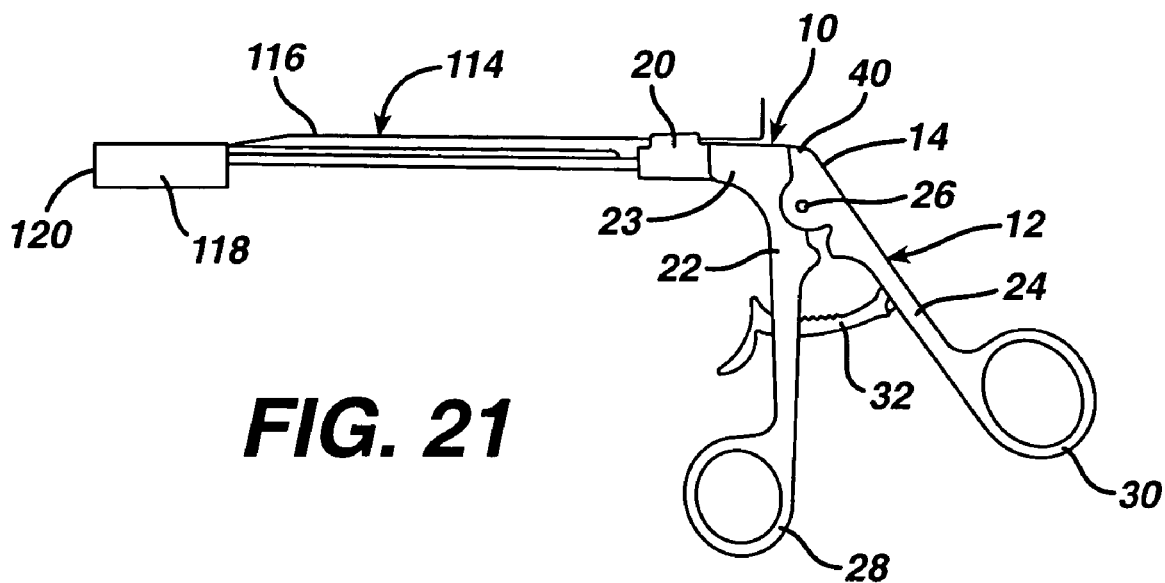
FIG. 21 is a side elevation of the instrument of FIGS. 1-6 shown in combination with an alternate implant protector.
Figure 22:
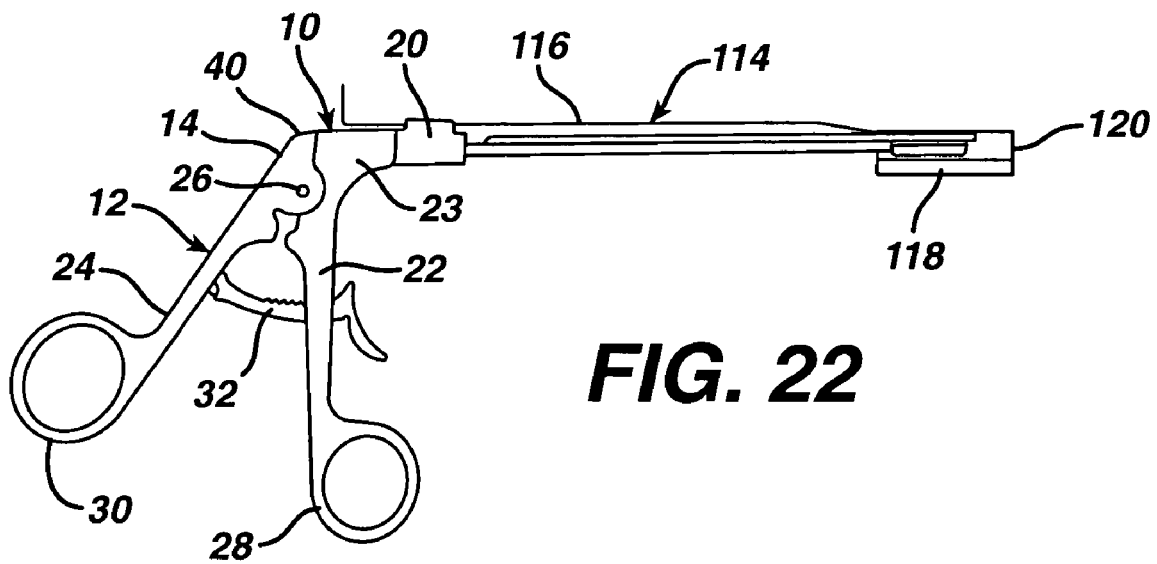
FIG. 22 is the opposite side elevation of the combination instrument and implant protector of FIG. 21.
Figure 23:
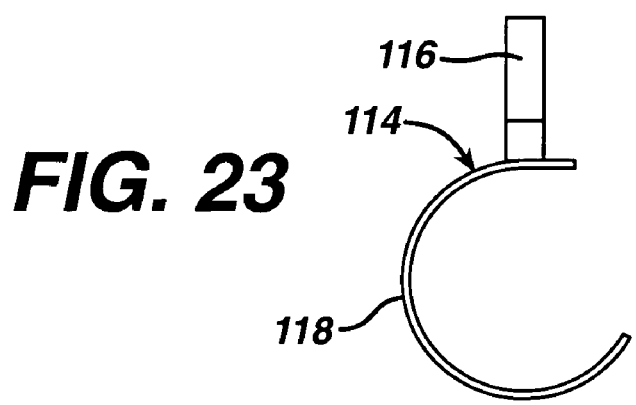
FIG. 23 is an end view of the implant protector of FIGS. 21-22.

Another implant protector 114 is illustrated in FIGS. 21-23. This implant protector 114 is used in conjunction with the delivery guide 20 illustrated mounted on the instrument 10 in FIGS. 1, 3, 21 and 22. This implant protector 114 comprises an elongate guide shaft 116 and an integral protector 118 at its distal end 120. A portion of the guide shaft 116 is received in a complementary channel on the top of the delivery guide 20 to mount the implant protector 114 to the instrument 10. The integral protector 118 is sized and shaped to substantially surround the curved portions 50, 80 of the instrument and an implant fixed between these curved portions 50, 80.

All of the implant protectors may be sized to fit through a standard arthroscopic portal. Typical arthroscopic portals have a length of about 8-12 mm. However, the surgical instrument 10 and implant protectors may also be used in a minimally invasive procedure, such as a mini-arthrotomy, as well as in an open arthrotomy or other orthopaedic surgical procedure. The instruments and protectors could have larger sizes for use in these other procedures. In addition, it should be understood that the present invention is not limited to any particular dimension unless expressly called for in the claims.

It will be appreciated that the structure of the first illustrated instrument 10 can be modified if desired. For example, parts shown as assembled may be made integral and parts shown as a single element may be constructed as assemblies. In addition, instead of providing curved end portions 50, 80, the end portions of the main shaft 16 and the slide rod 18 can be shaped to correspond with the shape of the implant if the implant is different from that shown in the drawings; for example, the distal ends 52, 82 of the main shaft 16 and slide rod 18 could be straight. By following the shape of the inner edge of the implant, the end portions of the main shaft and slide rod protect the inner edge of the implant from potential damage as the implant is introduced to the damaged tissue site.

Another embodiment of a surgical instrument illustrating the principles of the present invention is illustrated in FIGS. 24-32. The second illustrated instrument 210 includes a handle 212 at the proximal end 214, a main shaft 216 and a slide arm 218. The main shaft 216 and slide arm 218 extend from the handle 212 to the distal end 219 of the instrument 210.

The handle 212 of the second illustrated instrument 210 includes two arms 222, 224 connected together at a pivot 226. Each arm 222, 224 includes a grip portion 228, 230 that the surgeon squeeze to pivot the arms about pivot 226. As the grip portions 228, 230 are brought closer together, the slide arm 218 is moved from an open or unclamped position, shown in FIGS. 24-25, 29 and 31, to a closed or clamped position, shown in FIGS. 26-27, 30 and 32.

One arm 224 is integral with the main shaft 216 of the instrument 210. The other arm 222 is integral with the slide arm 218 of the instrument 210. When the grip portions 228, 230 of the arms 222, 224 are squeezed together, the top portion of the arm 222 and the integral slide arm 218 are moved in a generally distal direction. When the grip portions 228, 230 are released, a spring mechanism 232 urges the arms 222, 224 and the integral main shaft 216 and slide arm 218 to the open or unclamped position shown in FIGS. 24 and 25.

The slide arm 218 of the second illustrated instrument 210 has a distal end 252 illustrated in side elevation in FIG. 28. As there shown, the distal end 252 is tapered in side elevation. The height of the distal end 252 of the slide arm 218 gradually increases in the proximal direction. The top surface 235 of the distal end 252 of the slide arm 218 defines an angle α with the bottom surface 237 of the distal end 252 of the slide arm 218.

The main shaft 216 of the second illustrated instrument 210 has a distal end 282 that is smoothly curved, or bull-nosed in shape. The distal end 282 is shaped to define an enlarged well 283 that may receive part of an implant. The well 283 is open at its top facing the bottom surface 237 of the slide arm 218. The well 283 may be sized and shaped so that a substantial part of the implant is received within the well 283.

Figure 24:
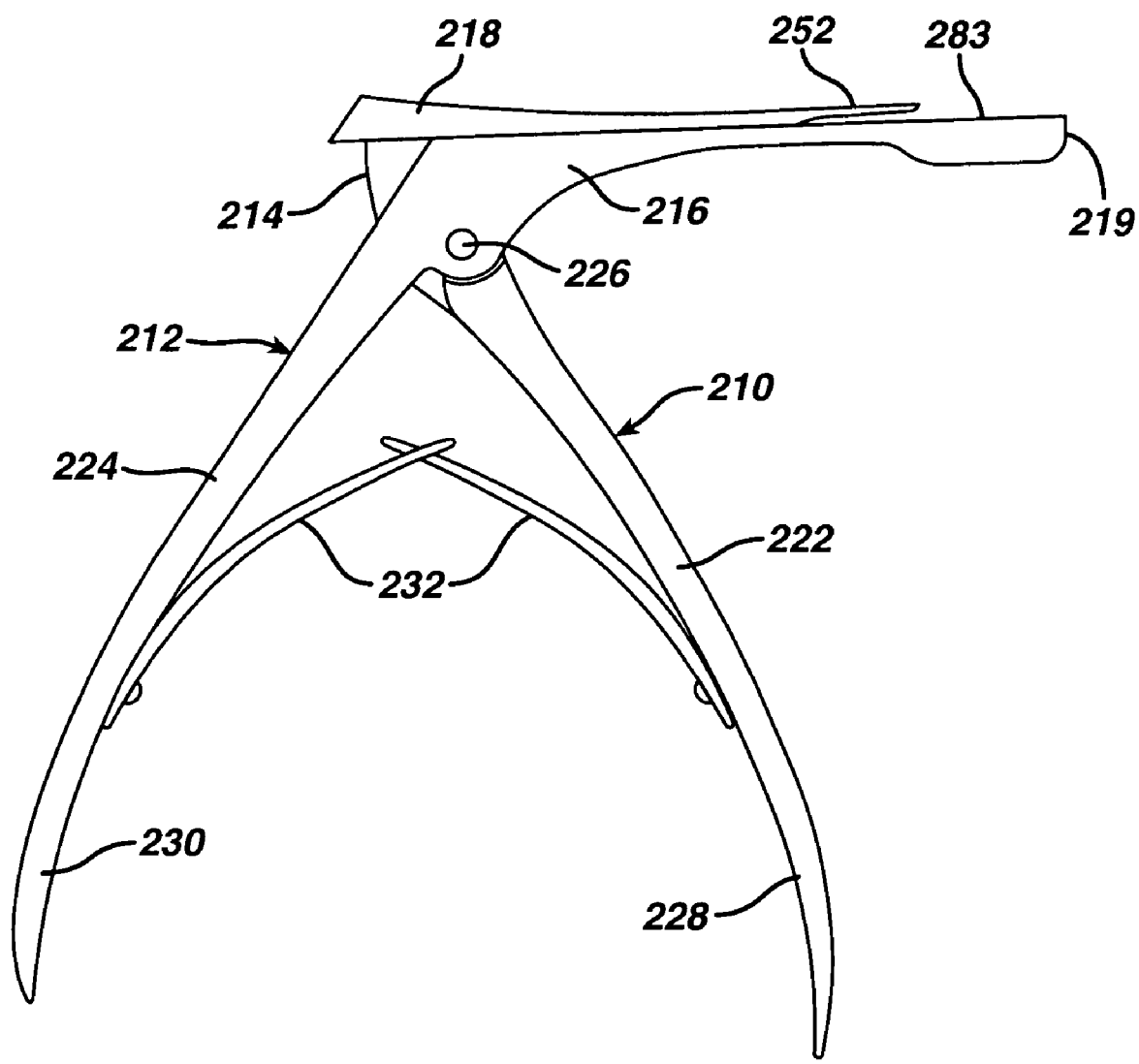
FIG. 24 is a side elevation or view of a second instrument illustrating the principles of the present invention, the instrument being shown in an open or unclamped position.
Figure 29:
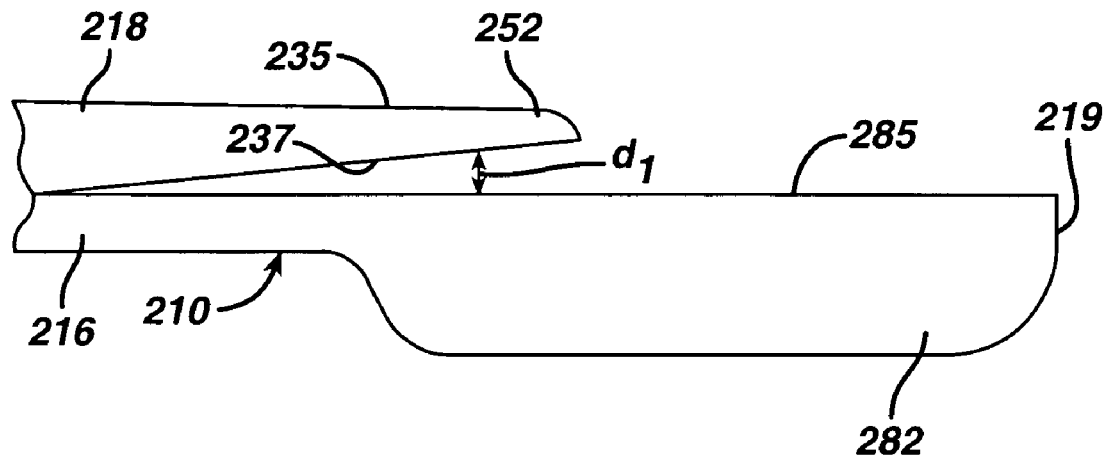
FIG. 29 is a side elevation of the distal end of the instrument of FIG. 24 shown in the open or unclamped position.

The minimum vertical distance between the bottom surface 237 of the slide arm 218 and the top surface 285 of the main shaft 216 surrounding the well 283 is shown in FIG. 29 at $d_1$. Generally, distance $d_1$ is greater than the thickness of the implant. Also as shown in FIGS. 24-25 and 29, a substantial part of the well 283 is exposed or uncovered when the instrument 210 is in the open or unclamped position.

Figure 30:
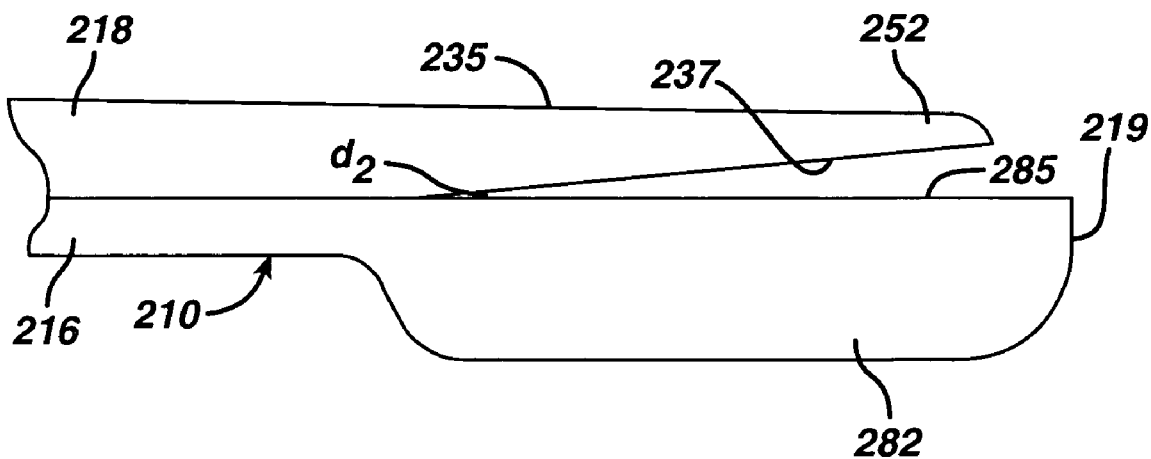
FIG. 30 is a perspective view of the distal end of the instrument of FIG. 24 shown in the closed or clamped position.

In contrast, when the instrument 210 is placed in the closed or clamped position, the minimum vertical distance between the bottom surface 237 of the slide arm 218 and the top surface 285 of the main shaft 216 surrounding the well 283 decreases substantially to the distance shown at $d_2$ in FIG. 30. Generally, distance $d_2$ is equal to or slightly less than the thickness of the implant. Also as shown in FIGS. 26-27 and 30, when a substantial part of the well 283 is covered by the distal end 252 of the slide arm 218 when the instrument 210 is in the closed or clamped position.

Figure 31:
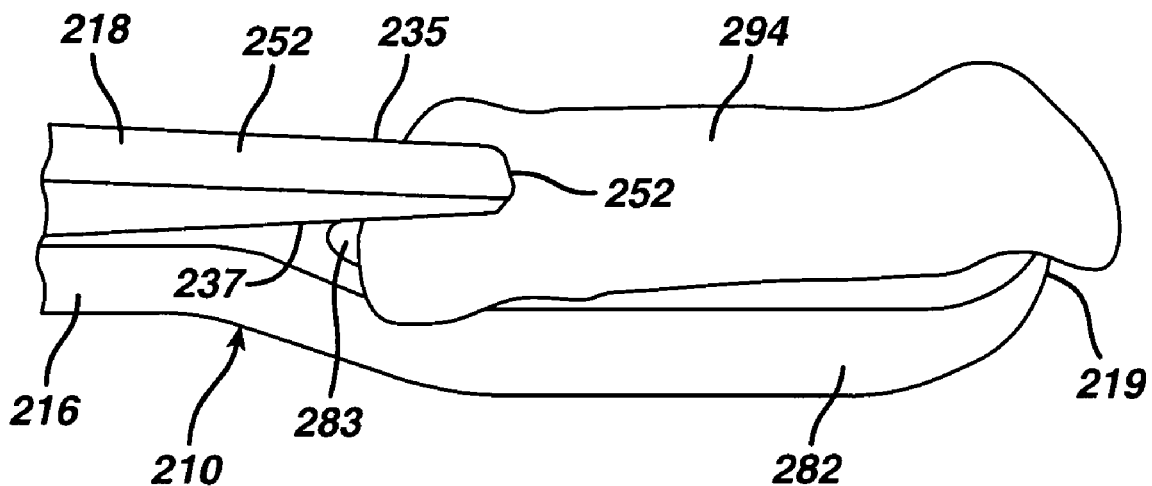
FIG. 31 is a perspective view of the distal end of the instrument of FIG. 24 similar to FIG. 29 but shown with an implant.
Figure 32:
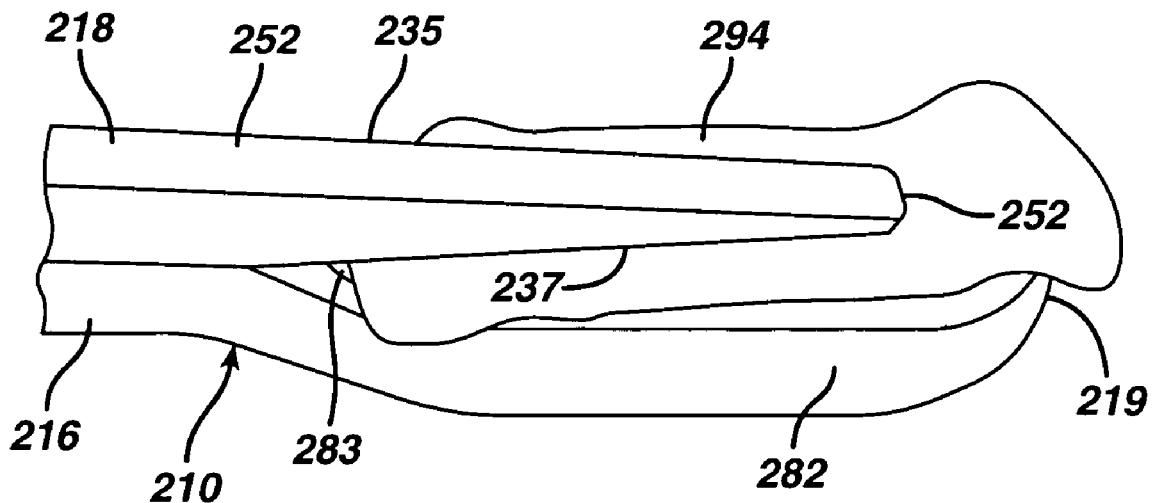
FIG. 32 is a side elevation of the distal end of the instrument of FIG. 24, similar to FIG. 30 but shown with an implant.

Thus, as shown in FIG. 31, when the instrument 210 is in the open or unclamped position, the implant 294 rests loosely on and in the well 283 at the distal end 282 of the main shaft 216 and the implant is substantially uncovered. When the instrument 210 is in the closed or clamped position a shown in FIG. 32, part of the implant 294 is secured or squeezed between the bottom surface 237 of the slide arm 218 and the top surface 285 of the main shaft 216 and the implant is substantially covered by the distal end of the slide arm 218. Only a small part of the periphery of the implant 294 is exposed. With the instrument 210 and implant 294 in the position shown in FIG. 32, the implant 294 will be substantially protected from damage as it is introduced to the damaged tissue site. The surgeon can use standard surgical procedures to introduce the implant using the second illustrated instrument 210, and may use the technique described above using implant protectors like those shown in FIGS. 19 and 20. However, with the second illustrated instrument 210, it may not be necessary to use separate implant protectors like those shown in FIGS. 19 and 20 since the distal end of the instrument 210 substantially encloses the implant to protect the implant from damage. In addition, if no implant protector is used, the bull-nose distal end of the second instrument 210 may be smooth and rounded to prevent cutting or abrasion of native tissue as the bull-nose distal end is moved through native tissue to deliver the implant.

An alternative distal end for the instrument of FIGS. 24-32 is shown in FIGS. 35-38. As there shown, the distal end of the main shaft could be open instead of bull-nosed as in the embodiment illustrated in FIGS. 24-32. The distal surfaces of the distal end of the main shaft may be finished to be smooth with no sharp edges to damage tissue as the instrument is introduced to the damaged tissue site. In FIGS. 35-38, the same reference numbers have been used as in FIGS. 24-32, followed by the letter "a" to indicate that FIGS. 35-38 is an alternative embodiment. The remaining features of the instrument of FIGS. 35-38 may be like those described above for the instrument of FIGS. 24-32.

With both the first and second illustrated instruments 10, 210, the distal end 52, 252 of the slide rod or arm 18, 218 is displaced in the proximal-distal direction as the instrument is moved between the open and closed position. In both of these instruments, the gap between the distal end 52, 252 of the slide rod or arm 18, 218 and the distal end 82, 282 of the main shaft 16, 216 decreases as the instrument is closed or clamped. In both of these instruments, the distal end of the slide rod or arm moves between the open and closed positions without pivoting. And in both of these instruments 10, 210, the maximum distance between the top surface of the distal end of the slide rod or arm and the bottom surface of the distal end of the main shaft can be made to be less than 12 mm so that the instrument can be used in arthroscopic surgery and so that the instrument can be opened to release the implant in a confined space, such as that present in a typical intra-articular site.

Figure 33:
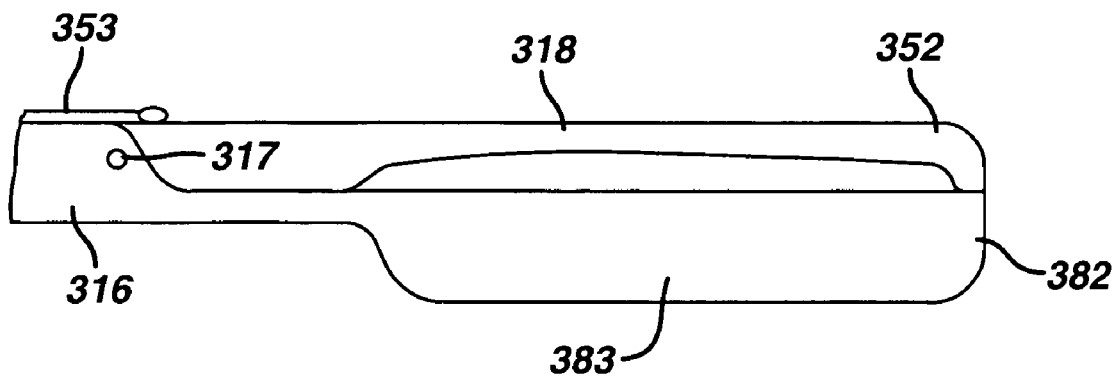
FIG. 33 is a side elevation of an alternative distal end for a surgical instrument shown in the closed position.
Figure 34:
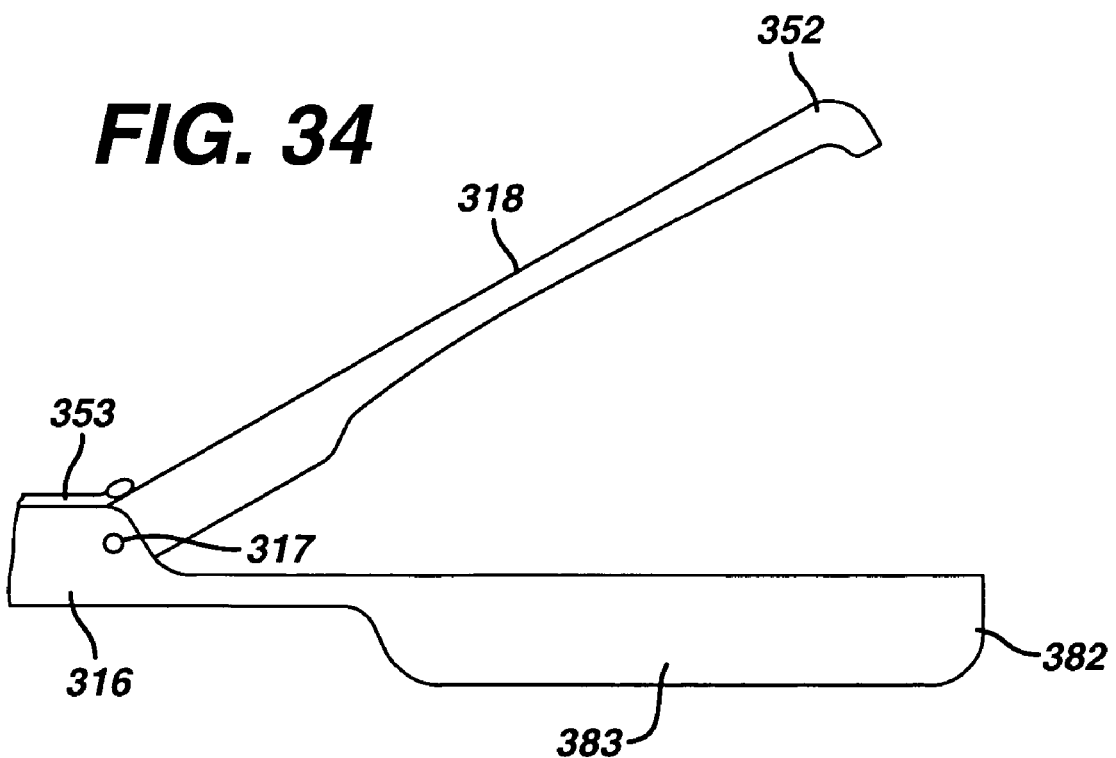
FIG. 34 is a side elevation of the alternative distal end for the surgical instrument shown in FIG. 33 but shown in the open position.
Figure 35:
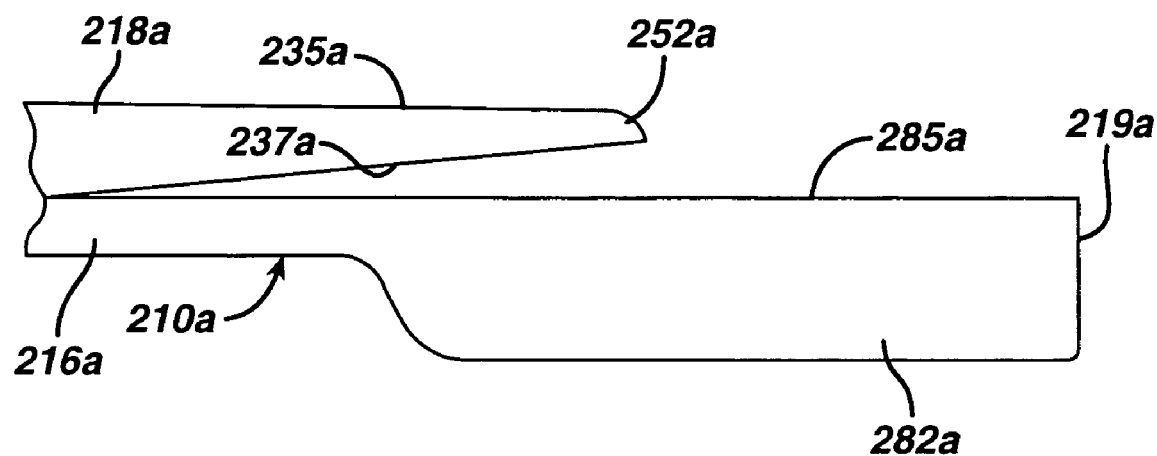
FIG. 35 is a side elevation for an alternative distal end for the surgical instrument of FIGS. 24-32, shown in the open or unclamped position.
Figure 36:
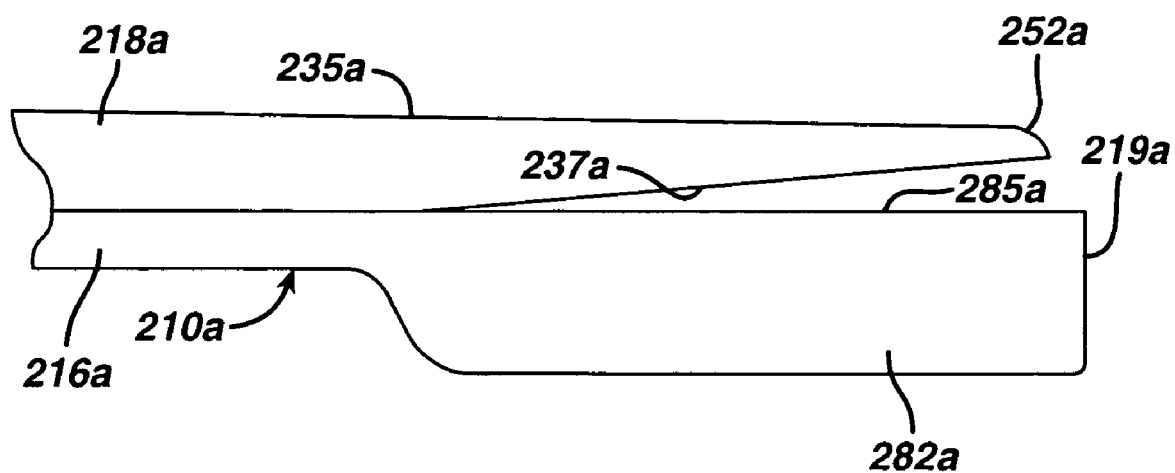
FIG. 36 is a side elevation similar to FIG. 35 but shown with the instrument in the closed or clamped position.
Figure 37:
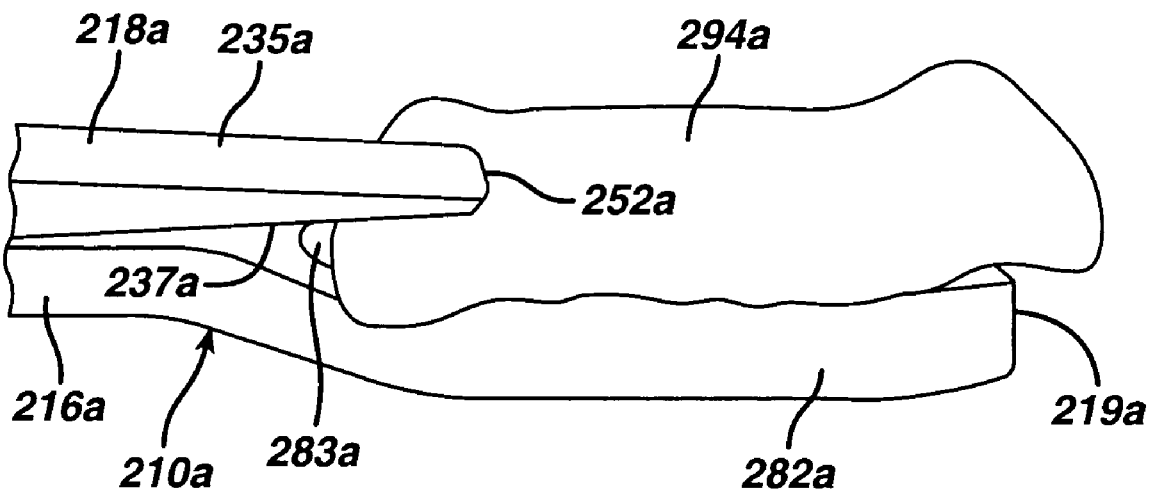
FIG. 37 is a perspective view of the alternative distal end of FIG. 35 but shown with an implant.
Figure 38:
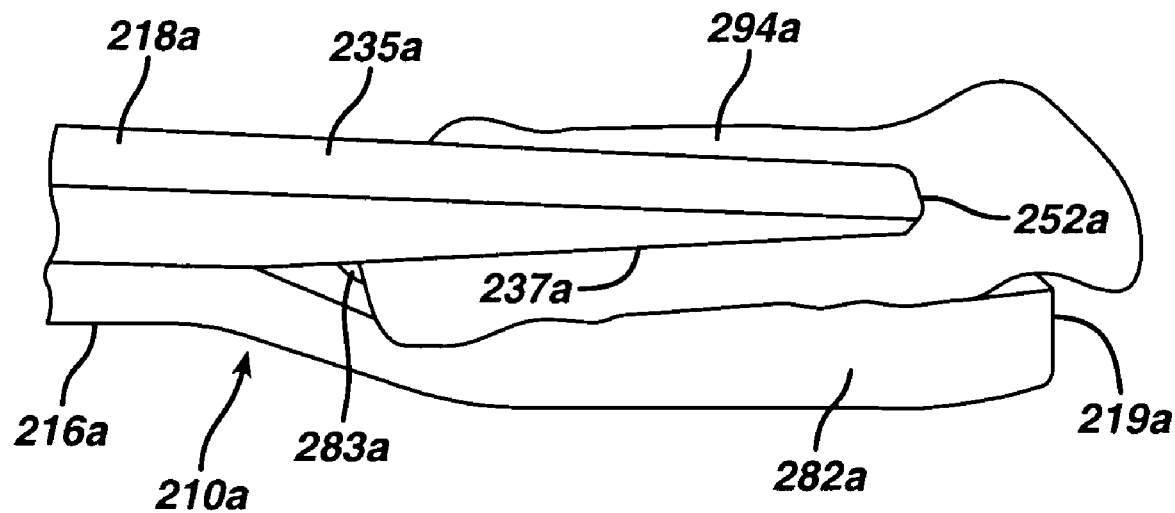
FIG. 38 is a perspective view of the alternative distal end of FIG. 36 but shown with an implant.

If the maximum dimension of the instrument is of less concern, the distal ends of the slide arm and main shaft may be modified from the structures described above. For example, as shown in FIGS. 33-34, a main shaft 316 could be provided with a distal end 382 shaped like that of the second instrument 210, with a bull-nosed end and an enlarged well 383. Instead of comprising a slide member, the top member could comprise a pivotable cover 318 at the distal end 352, connected to one of the arms (not shown) through an actuator cable 353 and to the main shaft 316 through a hinge pin 317. The design shown in FIGS. 33-34 should be suitable to protect the implant from damage as the implant is delivered to the damaged tissue site, since a substantial part of the implant can be received in the well 383 and since the implant will be substantially covered by the pivotable cover 318. In this embodiment, the distal surfaces of the main shaft 316 and pivotable cover 318 can be curved and smooth to prevent damage to native tissue as the implant is delivered.

All of the above illustrated instruments 10, 210 can be made of standard materials for surgical instruments. The implant protectors 104, 112 can also be made of standard materials, including surgical grade plastic such as ABS plastic.

Alternative designs for the delivery of implants to damaged tissue sites are disclosed in the following U.S. Patent Applications, filed concurrently herewith and incorporated by reference herein in their entireties: U.S. patent application Ser. No. 10/610,287 entitled "Slide and Kit for Delivering Implants," filed concurrently herewith by Thomas S. Camino, Anthony D. Zannis, John W. Kemppainen and Herbert E. Schwartz, and U.S. patent application Ser. No. 10/610,288 entitled "Implant Delivery Instrument," filed concurrently herewith by Anthony D. Zannis, Thomas S. Camino, John W. Kemppainen, Herbert E. Schwartz and Danny E. McAdams.

The present invention is expected to have particular utility in delivering orthopaedic implants to damaged joint sites, although it will be appreciated that the invention has broader applications. For example, the instrument of the present invention can also be used to deliver other types of implants to other damaged tissue sites in the body. The present invention could be used to deliver any type of tissue scaffold, patch, or graft (allograft, autograft or heterograft) to any type of tissue, and the illustrated embodiments may be modified if desired to allow for such use. Unless otherwise expressly limited, the claims should not be construed as being limited to the delivery of orthopaedic implants to damaged joint sites.

While only specific embodiments of the invention have been described and shown, it is apparent that various alternatives and modifications can be made thereto. Those skilled in the art will also recognize that certain additions can be made to the illustrative embodiments. It is, therefore, the intention in the appended claims to cover all such alternatives, modifications and additions as may fall within the true scope of the invention.

We claim:

1. A surgical instrument for delivering an implant to a damaged tissue site comprising:

a main shaft having a longitudinal axis, a proximal end and a distal end; and a slide member juxtaposed with the main shaft having a longitudinal axis, a proximal end and a distal end;

wherein:

the surgical instrument has open and closed positions;

the slide member is movable in a proximal-distal direction with respect to the main shaft to move the surgical instrument between the open and closed positions, the distal end of the slide member having an open position when the surgical instrument is in the open position and a closed position when the surgical instrument is in the closed position, the closed position of the distal end of the slide member being spaced from the open position of the distal end of the slide member in the proximal-distal direction;

there is a gap between the distal end of the slide member and the distal end of the main shaft when the instrument is in the open position;

there is a smaller gap between the distal end of the slide member and the distal end of the main shaft when the instrument is in the closed position;

the slide member and the main shaft include a slot and pin received within the slot for guiding the movement of the slide member, the slot defining an obtuse angle with the longitudinal axes of the slide member and the main shaft and defining a path of travel for the pin; and the pin is in one position in the slot when the instrument is in the closed position and in a second position in the slot when the instrument is in the open position, the two positions of the pin with respect to the slot being displaced in a proximal-distal direction and in a second direction.

2. The surgical instrument of claim 1 wherein the slide member is movable between the open position and closed position without pivoting the distal end of the slide member.

3. The surgical instrument of claim 1 wherein the distal end of the slide member is tapered.

4. The surgical instrument of claim 1 wherein the distal end of the slide member has a top surface and the distal end of the main shaft has a bottom surface and wherein the distance between the top surface of the slide member and the bottom surface of the main shaft is greater when the instrument is in the open position than when the instrument is in the closed position.

5. The surgical instrument of claim 4 wherein the maximum distance between the top surface of the slide member and the bottom surface of the shaft is less than 10 mm in both the open and closed positions.

6. A surgical instrument for delivering an implant to a damaged tissue site comprising:

a main shaft having a proximal end and a distal end and walls shaped to define a well for receiving a substantial portion of the implant at the distal end, the walls defining the well having top edges lying in a plane across the top of the well, the well having a proximal-distal dimension; and a slide member having a proximal end and a distal end, the slide member being movable in a proximal-distal direction between a position substantially overlying the well to protect the implant to another position wherein a substantial part of the well is exposed;

wherein:

the slide member is tapered from a most narrow dimension at the distal end of the slide member to a wider dimension spaced proximally from the distal end; and when the slide member is in the position substantially overlying the well, a tapered gap is present between the slide member and the plane of the top of the well along the majority of the proximal-distal dimension of the well, the tapered gap being most narrow nearest the proximal end of the well, the gap continuously increasing in a distal direction and being greatest at the distal end of the slide member.

\* \* \* \* \*